(12) United States Patent
Ali

(10) Patent No.: US 12,409,250 B2
(45) Date of Patent: Sep. 9, 2025

(54) BIOVESSELS FOR USE IN TISSUE ENGINEERING

(71) Applicant: BioSapien Inc., New York, NY (US)

(72) Inventor: Khatija Pinky Ali, San Diego, CA (US)

(73) Assignee: BioSapien Inc., New York, NY (US)

( * ) Notice: Subject to any disclaimer, the term of this patent is extended or adjusted under 35 U.S.C. 154(b) by 751 days.

(21) Appl. No.: 17/521,384

(22) Filed: Nov. 8, 2021

(65) Prior Publication Data

US 2022/0233749 A1 Jul. 28, 2022

Related U.S. Application Data

(63) Continuation of application No. 16/570,231, filed on Sep. 13, 2019, now Pat. No. 11,197,945.

(60) Provisional application No. 62/731,564, filed on Sep. 14, 2018.

(51) Int. Cl.
| | |
|---|---|
| A61L 27/36 | (2006.01) |
| A61F 2/06 | (2013.01) |
| A61L 27/18 | (2006.01) |
| A61L 27/58 | (2006.01) |
| B33Y 10/00 | (2015.01) |

(52) U.S. Cl.
CPC ............ *A61L 27/3633* (2013.01); *A61F 2/06* (2013.01); *A61L 27/18* (2013.01); *A61L 27/58* (2013.01); *B33Y 10/00* (2014.12); *A61F 2002/061* (2013.01); *A61F 2002/065* (2013.01)

(58) Field of Classification Search
None
See application file for complete search history.

(56) References Cited

U.S. PATENT DOCUMENTS

| | | | |
|---|---|---|---|
| 5,292,802 A | 3/1994 | Rhee et al. | |
| 5,405,325 A | 4/1995 | Labs | |
| 7,332,160 B2 | 2/2008 | Freyman et al. | |
| 8,512,622 B2 | 8/2013 | Cho et al. | |
| 9,050,180 B1 | 6/2015 | Kong et al. | |
| 9,238,791 B2* | 1/2016 | Yoshioka | C12M 47/04 |
| 9,242,027 B2 | 1/2016 | Bellan et al. | |
| 2006/0085063 A1 | 4/2006 | Shastri et al. | |
| 2008/0085544 A1 | 4/2008 | Morita et al. | |
| 2009/0043373 A1* | 2/2009 | Arnault De La Menardiere | A61F 2/848 623/1.35 |
| 2009/0248145 A1 | 10/2009 | Chan et al. | |

(Continued)

FOREIGN PATENT DOCUMENTS

| | | | |
|---|---|---|---|
| JP | 2008067921 A | * | 3/2008 |
| JP | 2010517703 A | | 5/2010 |

(Continued)

OTHER PUBLICATIONS

Machine translation JP2008067921A (Year: 2008).*

(Continued)

*Primary Examiner* — Abbas Rashid
*Assistant Examiner* — Wayne K. Swier
(74) *Attorney, Agent, or Firm* — WILSON SONSINI GOODRICH & ROSATI

(57) ABSTRACT

Described herein are bioengineered constructs and methods of producing the same. The constructs and methods disclosed herein can be applied towards, for example, the generation of vascular grafts to treat cardiovascular disease.

21 Claims, 8 Drawing Sheets

(56) References Cited

U.S. PATENT DOCUMENTS

| | | |
|---|---|---|
| 2010/0057196 A1 | 3/2010 | Pathak |
| 2011/0033933 A1 | 2/2011 | Gharib et al. |
| 2015/0094796 A1 | 4/2015 | Matheny |
| 2015/0359619 A1 | 12/2015 | Lelkes et al. |
| 2016/0228233 A1* | 8/2016 | Winkler ............ A61F 2/06 |
| 2017/0136156 A1 | 5/2017 | Walls |
| 2018/0037870 A1 | 2/2018 | Cho et al. |
| 2018/0078677 A1 | 3/2018 | Cho et al. |
| 2018/0110901 A1 | 4/2018 | Lewis et al. |
| 2018/0235634 A1 | 8/2018 | Kassab et al. |

FOREIGN PATENT DOCUMENTS

| | | | |
|---|---|---|---|
| JP | 2016530899 A | 10/2016 | |
| WO | WO-2008098252 A2 | 8/2008 | |
| WO | WO-2015040139 A1 | 3/2015 | |
| WO | WO-2016054847 A1 * | 4/2016 | ............ A61F 2/02 |
| WO | WO-2020056248 A1 | 3/2020 | |

OTHER PUBLICATIONS

Machine translation WO2016054847A1 (Year: 2016).*
Alajati et al., Spheriod-based engineering of a human vasculature in mice, Nature, Nature Methods, 2008, vol. 5 (5), p. 439-445.
Anwar et al., 3D Printing is a Transformative Technology in Congenital Heart Disease, JACC: Basic to Translational Science, 2018, vol. 3 (2), p. 294-312.
Arevalos et al., Regulation of valve endothelial cell vasculogenic network architectures with ROCK and Rac inhibitors, Microvasc Res., 2015, vol. 98, p. 108-118.
Bishop et al., 3-D bioprinting technologies in tissue engineering and regenerative medicine: Current and future trends, Elsevier, Genes & Diseases, 2017, vol. 4, p. 185-195.
Borovjagin et al., From Microscale Devices to 3D Printing: Advances in Fabrication of 3D Cardiovascular Tissues, Circ Res., 2017, vol. 120, p. 150-165.
Campos et al., Three-dimensional printing of stem cell-laden hydrogels submerged in a hydrophobic high-density fluid, Biofabrication,2013, vol. 5, p. 1758-5082.
Cheung et al., Current Progress in Tissue Engineering of Heart Valves: Multiscale Problems, Multiscale Solutions, Expert Opin Biol Ther., 2015, vol. 15 (8), p. 1155-1172.
Cho et al., Nanogels for Pharmaceutical and Biomedical Applications and Their Fabrication Using 3D Printing Technologies, Materials, 2018, vol. 11 (302), p. 1-15.
Colunga et al., Building Blood Vessels with Vascular Progenitor Cells, Trends Mol Med., 2018, vol. 24 (7), p. 630-641.
Cui et al., 3D Bioprinting for Organ Regeneration, Adv Healthc Mater 6 (1):1-54 (2017).
Dong et al., 3D-Printed Poly(E-caprolactone) Scaffold Integrated with Cell-laden Chitosan Hydrogels for Bone Tissue Engineering, Nature, Scientific Reports, 2017, vol. 7, p. 1-9.
Duan et al., 3D Bioprinting of heterogeneous aortic conduits with alginate/gelatin hydrogels, Society For Biomaterials, 2012, p. 1-10.
Duan et al., 3D Printed Trileaflet Valve Conduits Using Biological Hydrogels and Human Valve Interstitial Cells, Acta Biomater, 2014, vol. 10 (5), p. 1836-1846.
Elomaa et al., Additive Manufacturing of Vascular Grafts and Vascularized Tissue constructs, Tissue Engineering, vol. 23 (5), 2017, p. 436-450.
Fan et al., Bio-printing cell-laden Matrigel-agarose constructs, J Biomater Appl., 2016, vol. 31 (5), p. 684-692.
Gao et al., Optimization of gelatin-alginate composite bioink printability using rheological parameters: a systematic approach, Biofabrication, 2019, vol. 10 (3), p. 1-17.
Gopinathan et al., Recent trends in bioinks for 3D printing, Biomaterials Research, 2018, vol. 22 (11), p. 1-15.
Graham et al., High-Resolution Patterned Cellular Constructs by Droplet-Based 3D Printing, Nature, Scientific Reports, 2017, vol. 7, p. 1-11.

Gross et al., Evaluation of 3D Printing and Its Potential Impact on Biotechnology and the Chemical Sciences, Analytical Chemistry, 2014, vol. 86, p. 3240-3253.
International Preliminary Report on Patentability dated Mar. 9, 2021 for International Application Serial No. PCT/US2019/051001.
International Search Report and Written Opinion dated Feb. 4, 2020 for International Application Serial No. PCT/US2019/051001.
Jammalamadaka et al., Recent Advances in Biomaterials for 3D Printing and Tissue Engineering, Journal of Functional Biomaterials, 2018, vol. 9 (22), p. 1-14.
Jang et al., 3D Bioprinting and In Vitro Cardiovascular Tissue Modeling, Bioengineering, 2017, vol. 4 (71), p. 1-20.
Jia et al., Direct 3D bioprinting of perfusable vascular constructs of using a blend bioink, Biomaterials, 2016, vol. 106, p. 58-68.
Kang et al., Optimizing Photo-encapsulation Viability of Heart Valve Cell Types in 3D Printable Composite Hydrogels, Ann Biomed Eng., 2017, vol. 45 (2), p. 360-377.
Kim et al., Blended PCL/PLGA scaffold fabrication using multi-head deposition system, Microelectronic Engineering, 2009, vol. 86, p. 1447-1450.
Kolesky et al., 3D Bioprinting of Vascularized, Heterogeneous Cell-Laden Tissue Constructs, Advanced Material, Adv. Mater, 2014, vol. 26, p. 3124-3130.
Lee et al., Printing of Three-Dimensional Tissue Analogs for Regenerative Medicine, Ann Biomed Eng., 2017, vol. 45 (1), p. 115-131.
Li et al., Additive Manufacturing of Biomedical Constructs with Biomimetic Structural organizations, Materials, 2016, vol. 9 (909), p. 1-17.
Li et al., Recent advances in bioprinting techniques: approaches, applications and future prospects, J Transl Med, 2016, vol. 14 (271), p. 1-15.
Maitz et al., Applications of synthetic polymers in clinical medicine, Biosurface and Biotribology, 2015, vol. 1, p. 161-176.
Mallone et al., Cardiovascular Regenerative Technologies: Update and Future Outlook, Transfus Med Hemother, 2016, vol. 43, p. 291-296.
Mandrycky et al., 3D Bioprinting for Engineering Complex Tissues, Biotechnol Adv., 2016, vol. 34 (4), p. 422-434.
Mao et al., Regenerative medicine: Current therapies and future directions, Special Feature: Perspective, 2015, vol. 112 (47), p. 14452-14459.
Rattanakit et al., Extrusion printed polymer structures: A facile and versatile approach to tailored drug delivery platforms, International Journal of Pharmaceutics, 2012, p. 254-263.
Ravi et al., Biomaterials for vascular tissue engineering, Regen Med. Auther manuscript, 2010, vol. 5(1): 107, p. 1-21.
Schöneberg et al., Engineering biofunctional in vitro vessel models using a multilayer bioprinting technique, Nature, Scientific Reports, 2017, vol. 8, p. 1-13.
Shim et al., Three-Dimensional Printing of Antibiotics-Loaded Poly-ε-Caprolactone/Poly(Lactic-Co-Glycolic Acid) Scaffolds for Treatment of Chronic Osteomyelitis, TERM, p. 1738-2696.
Song et al., Vascular Tissue Engineering: Progress, Challenges, and Clinical Promise, Cell Stem Cell, 2018, p. 340-354.
Stratton et al., Polymeric 3D Printed Structures for Soft-Tissue Engineering, J Appl Polym Sci., 2018, vol. 135 (24), p. 1-30.
Tappa et al., Novel Biomaterials Used in Medical 3D Printing Techniques, Journal of Functional Biomaterials, 2018, vol. 9 (17), p. 1-16.
Valentin et al., Stereolithographic Printing of Ionically-Crosslinked Alginate Hydrogels for Degradable Biomaterials and Microfluidics, Lab Chip., 2017, vol. 17 (20), p. 3474-3488.
Van Der Valk et al., Engineering a 3D-Bioprinted Model of Human Heart Valve Disease Using Nanoindentation-Based Biomechanics, Nanomaterials, 2018, vol. 8 (296), p. 1-21.
Ventola et al., Medical Applications for 3D Printing: Current and Projected Uses, P&T, vol. 39(10), 2014, p. 704-711.
Wu et al., Bioprinting three-dimensional cell-laden tissue constructs with controllable degradation, Nature, Scientific Reports, 2015, vol. 6, p. 1-10.

(56) References Cited

OTHER PUBLICATIONS

Yu et al., Evaluation of Cell Viability and Functionality in Vessel-like Bioprintable Cell-Laden Tubular Channels, Journal of Biomechanical Engineering, 2013, vol. 135, p. 1-9.

Zehnder et al., Fabrication of Cell-Loaded Two-Phase 3D Constructs for Tissue Engineering, Materials, 2016, vol. 9 (887), p. 1-17.

Zhang et al., 3D Bioprinting for Tissue and Organ Fabrication, Ann Biomed Eng., 2017, vol. 45 (1), p. 148-163.

Zhang et al., Application of Hydrogels in Heart Valve Tissue Engineering, J Long Term Eff Med Implants, 2015, vol. 25, p. 105-134.

Zhang et al., Microfluidic Bioprinting for Engineering Vascularized Tissues and Organoids, Journal of Visualized Experiments, 2017, vol. 126, p. 1-8.

\* cited by examiner

BIOVESSELS FOR USE IN TISSUE ENGINEERING

CROSS REFERENCE

This Application is a Continuation of U.S. application Ser. No. 16/570,231 filed Sep. 13, 2019, now U.S. Pat. No. 11,197,945, which claims the benefit of U.S. Provisional Application No. 62/731,564 filed Sep. 14, 2018, each of which is incorporated herein by reference in its entirety.

BACKGROUND

Cardiovascular disease is the leading cause of death worldwide. In some instances, cardiovascular disease can be treated with vascular grafts, which can improve blood flow to organs supplied by a diseased or damaged blood vessel. Vascular grafts can rely on transplantation using allograft materials, which can cause immunogenicity. Thus, alternative methods to prepare vascular grafts could be beneficial for patients suffering from cardiovascular disease.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

In some embodiments, the disclosure provides a vascular graft comprising a cylindrical hollow body, wherein the cylindrical hollow body comprises a first opening and a second opening, and wherein the cylindrical hollow body comprises: (a) a primary channel, wherein the primary channel comprises an inner wall and an outer wall with a void space between the inner wall and the outer wall, wherein the inner wall and the outer wall are composed of a polymer; and (b) a viable cell-infused extracellular matrix disposed within the void space, and wherein the void space contains a microstructure containing a plurality of microchannels.

In some embodiments, the disclosure provides a vascular graft, the vascular graft comprising a cylindrical hollow body, wherein the cylindrical hollow body comprises a first opening and a second opening, and wherein the cylindrical hollow body comprises: (a) a primary channel, wherein the primary channel comprises an inner wall and an outer wall with a void space between the inner wall and the outer wall, wherein the inner wall and the outer wall are composed of a polymer; and (b) a viable cell-infused extracellular matrix disposed within the void space, and wherein the void space contains a microstructure containing a plurality of microchannels, wherein the vascular graft is submerged in a media that promotes growth of the cells in the viable cell-infused extracellular matrix.

In some embodiments, the disclosure provides a method of increasing flow of a biological fluid in a vessel in a subject in need thereof, the method comprising implanting a vascular graft in the subject, wherein the vascular graft comprises a cylindrical hollow body, and wherein the cylindrical hollow body comprises: (a) a primary channel, wherein the primary channel comprises an inner wall and an outer wall with a void space between the inner wall and the outer wall, wherein the inner wall and the outer wall are composed of a polymer; and (b) a viable cell-infused extracellular matrix disposed within the void space, and wherein the void space contains a microstructure containing a plurality of microchannels, wherein implantation of the vascular graft in the subject increases flow of the biological fluid in the vessel of the subject.

In some embodiments, the disclosure provides a method of printing a vascular graft, the method comprising: (a) depositing onto a substrate a polymer to form an inner wall; (b) depositing onto the inner wall a viable cell-infused extracellular matrix; (c) depositing onto the viable cell-infused extracellular matrix the polymer to form an outer wall, wherein the depositing of steps (a), (b), and (c) forms a cylindrical hollow body, wherein the cylindrical hollow body comprises a first opening and a second opening, and wherein the cylindrical hollow body comprises a primary channel, wherein the primary channel comprises the inner wall and the outer wall; and wherein the vascular graft is printed to provide a microstructure containing a plurality of microchannels in the void space.

DETAILED DESCRIPTION

Figure 1:
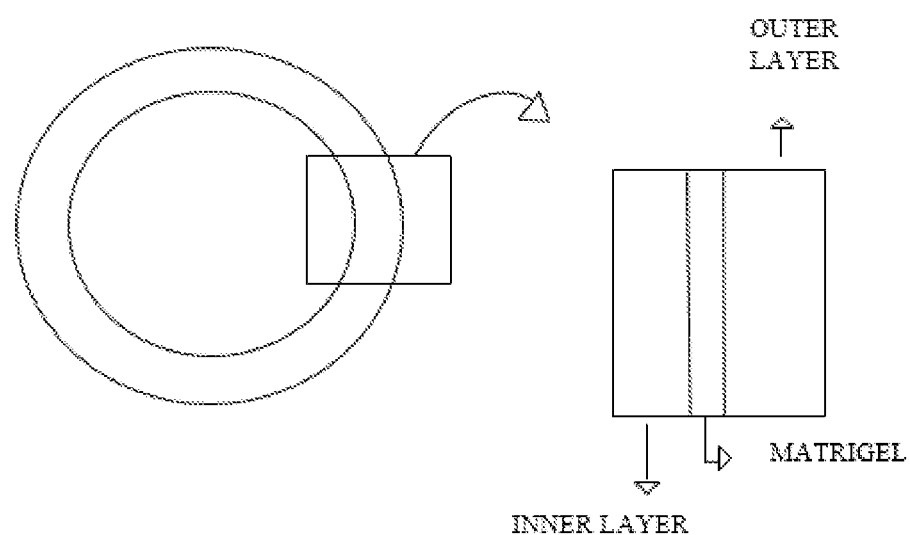
FIG. 1 depicts a cross-sectional view of the primary channel of a vascular construct. The inset on the right is a magnified view to show the structure of the channel wall.

Described herein are vascular grafts and methods of making the same. A vascular graft of the disclosure can mitigate a condition by restoring the proper flow of biological fluids to a tissue. For example, a vascular graft disclosed herein can be used in the treatment of diseases/disorders such as cardiovascular disease, cerebrovascular disease, lymphatic vasculature disease, ocular disease, edemas, pulmonary disease, and urinary tract disorders. Non-limiting examples of vessels that can be integrated or connected with a vascular graft of the disclosure include blood vessels, lymphatic vessels, Schlemm's canal, ureters, urethras, tear ducts, and airway passages. In some embodiments, a vascular graft disclosed herein aids in the transport of fluid. Non-limiting examples of fluids that can be transported through vascular graft of the disclosure include blood, lymphatic fluid, cerebrospinal fluid, urine, semen, air, tears, bile, aqueous humor, saliva, and breast milk.

Cardiovascular Disorders.

A vascular graft disclosed herein can treat, for example, cardiovascular disease. Cardiovascular disease encompasses a wide range of disease affecting the heart or blood vessels. The sub-type of cardiovascular disease affecting blood vessels is known as vascular disease. The presence of vascular disease can lead to decreased blood flow to target tissues, which can subsequently lead to tissue damage. Non-limiting examples of vascular diseases that can be treated using a vascular graft disclosed herein include coronary artery disease, cerebrovascular disease, renal artery stenosis, erythromelalgia, Buerger disease, and atherosclerosis.

The underlying mechanisms and symptoms of vascular disease can vary depending on the type of disease. Coronary artery disease can be caused by a reduction of blood flow to the heart muscle due to a build up of plaque in the arteries of the heart. There are multiple types of coronary artery disease including, for example, stable angina, unstable angina, myocardial infarction, and sudden cardiac death. Symptoms of coronary artery disease can include pain in the chest, shoulder, arm, back, neck, or jaw, and shortness of breath.

Cerebrovascular disease can be caused by abnormal blood flow in vessels supplying the brain. Abnormal blood flow can be caused by, for example, arteriovenous malformations (abnormal tangles of blood vessels), blood vessel rupture, accumulation of protein within blood vessels, aneurysm rupture, atherosclerosis, thrombosis, or blood vessel narrowing. Inadequate blood flow to brain cells can result in a stroke leading to cell death. Symptoms of cerebrovascular disease can include, for example, weakness of one side of the face or body, balance difficulties, cognitive decline, altered speech, vomiting, neck stiffness, migraines, and seizures.

Renal artery stenosis can result from narrowing the renal arteries and can be caused by atherosclerosis or fibromuscular dysplasia, a non-atherosclerotic, non-inflammatory disorder causing abnormal growth within the wall of an artery. Renal stenosis can lead to decreased blood flow to the kidney. Decreased blood flow to the kidney can cause changes to kidney structure, an abnormal glomerular filtration rate, and kidney failure.

Erythromelalgia is a disorder in which blood vessels, often in the extremities, are episodically blocked. Episodically blocked blood vessels can then become hyperemic and inflamed. Symptoms of erythromelalgia include, for example, a painful burning sensation in the extremities, swelling, Buerger disease involves progressive inflammation and thrombosis of blood vessels of the hands and feet. Buerger disease can result in pain of the extremities and lead to ulcerations and gangrene which can result in a need for amputation of extremities.

Atherosclerosis can be caused by high levels of low-density lipoprotein (LDL) in the blood. High LDL levels can result in the build up of plaque within arteries leading to a blockage of blood flow. Depending on the blood vessels affected, atherosclerosis can lead to many other disorders including cardiovascular disease and cerebrovascular disease.

Treatment of Vascular Disease

A vascular disease can be treated using a vascular graft described herein. Vascular grafts can redirect blood flow from one area to another by reconnecting blood vessels. For example, a vascular graft can be used to bypass around a diseased or blocked blood vessel, from an area of relatively normal blood flow to another area of relatively normal blood flow. Bypassing blocked or diseased vessels can restore blood flow to a tissue and serve as a treatment for vascular disease. In some embodiments, a vascular graft disclosed herein can be used to bypass an area of stenosis in a blood vessel.

Vascular grafts can be derived from a subject's own blood vessels (autograft) or from a donor blood vessel (allograft). Use of an autograft involves the creation of a second surgical site in a subject, while allografts can come with immunogenicity concerns and are not always readily available. These issues of autografts and allografts can be overcome by synthetic vascular grafts comprising biocompatible polymers.

In some embodiments, a vascular graft disclosed herein is used to treat a vascular disease. For example, a vascular graft of the disclosure can be used to bypass a blocked or damaged blood vessel by connecting two areas of relatively normal blood flow. Non-limiting examples of blood vessels vascular grafts of the disclosure can connect include, for example, arteries, veins, arterioles, venules, elastic arteries, distributing arteries, capillaries, venules, sinusoids, and any combination thereof. In some embodiments, a vascular graft of the disclosure connects two lymphatic vessels. Vascular grafts of the disclosure can restore, increase, or control the flow of fluid such as blood or lymphatic fluid to, for example, the heart, brain, lungs, kidney, spleen, liver, pancreas, gall bladder, stomach, intestine, arms, legs, feet, hands, fingers, toes, skin, penis, vagina, ovaries, breast, muscles, eyes, nose, and esophagus.

Vascular Grafts

In some embodiments, a vascular graft disclosed herein comprises a cylindrical hollow body with a first opening and a second opening located at two ends of the hollow body. The cylindrical hollow body can comprise one or more channels, including a primary channel. The primary channel can comprise a lumen formed by a channel wall. The channel wall can comprise an inner wall and an outer wall to form a void space within the wall of the primary channel. In some embodiments, the primary channel is bifurcated into two or more secondary channels. In some embodiments, the primary channel splits into 1, 2, 3, 4, 5, 6, 7, 8, 9, 10, 11, 12, 13, 14, 15, or more secondary channels. In some embodiments, secondary channels can comprise channel walls with an inner wall and an outer wall forming a void space. In some embodiments, the channel walls comprise microchannels. Microchannels can, in some instances, provide an additional flow path for fluid through a vascular graft.

In some embodiments, primary channels, secondary channels, and components thereof comprise a polymeric material. Non-limiting examples of polymeric materials include polyesters, poly(alpha-hydroxy acids), polylactones, polyorthoesters, polycarbonates, polyanhydrides, polyphosphazenes, polycaprolactone (PCL), poly lactic acid (PLA), poly L-lactide-glycolic acid (PLGA), poly ethylene glycol diacrylate (PEGDA), polyethylene glycol (PEG), poly(hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, and PEG-glycolide.

Polymeric materials disclosed herein can be biocompatible and/or biodegradable. Biocompatible materials can remain present in the body without causing harm. Biodegradable materials can break down within the body without causing harm. Further, a biodegradable material can form degradation products that are not harmful. In some embodiments, a vascular graft disclosed herein comprises a biocompatible polymeric material. In some embodiments, a vascular graft disclosed herein comprises a biodegradable polymeric material.

The void space of a primary or secondary channel can be filled with, for example, an extracellular matrix (ECM) material. Non-limiting examples of ECM materials include Matrigel®, a basement membrane substrate, carrageenan, carbopol, chitosan, sodium alga acid, collagen I, collagen III, collagen IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, collagen type XXVI, collagen type XXVII, collagen type XXVIII, collagen type XXIX, chondroitin sulfate, dextrose, fibrin, fibrinogen, gelatin, gelose, gelatin methacrylate, hyaluronic acid, heparin sulfate, laminin, polyethylene glycol, a glycosaminoglycan (GAG), a proteoglycan, or a combination thereof. In some embodiments, the ECM material is seeded with cells.

In some embodiments, the void space of a channel wall comprises a microstructure containing a plurality of cylindrical tubes. Microstructure forming cylindrical tubes can be arranged in a pattern to form a microstructure. For example, cylindrical tubes can be arranged in a circular, triangular, rectangular, pentagonal, hexagonal, heptagonal, or octagonal pattern. In some embodiments, sub-structures can be present inside cylindrical tubes. Sub-structures can be, for example, triangular, rectangular, pentagonal, hexagonal, heptagonal, or octagonal. In some embodiments, sub-structures comprise an ECM material such as any ECM material disclosed herein. ECM material can be infused with living cells. In some embodiments, the walls of cylindrical tubes forming a microstructure can comprise microchannels.

A vascular graft disclosed herein can comprise living cells. The presence of living cells in a vascular graft can facilitate the incorporation of the graft into the surrounding tissue following implantation. In some embodiments, a sub-structure inside cylindrical tubes of a microstructure comprises cells. In some embodiments, a void space of a channel wall is filled with 1, 2, 3, 4, 5, 6, 7, 8, 9, 10, 11, 12, 13, 14, 15 or more layers of cells. In some embodiments, an inner or outer wall of a channel wall is filled with 1, 2, 3, 4, 5, 6, 7, 8, 9, 10, 11, 12, 13, 14, 15 or more layers of cells. For example, a void space or a channel wall can comprise a layer of fibroblast cells, a layer of smooth muscle cells, and a layer of endothelial cells.

In some embodiments, a vascular graft or a precursor thereof comprises a spheroid of cells attached to the distal end of a branch that is connected to a primary channel of the vascular graft or a precursor thereof at the proximal end of the branch. The branch can comprise a cylindrical wall that defines a hollow core of the branch. In some embodiments, the cylindrical wall of the branch comprises a polymeric material such as any polymeric material disclosed herein. In some embodiments, the cylindrical wall of the branch surrounds a central core of extracellular matrix material such as any ECM material disclosed herein. Additionally, the central core of a branch can comprise a mixture of an ECM material and a polymeric material such as any polymeric material disclosed herein.

Non-limiting examples of cells that can be included in a graft of the disclosure include chondrogenic cells, chondrocytes, chondroprogenitor cells, chondrogenic precursors, keratinocytes, hair root cells, hair shaft cells, hair matrix cells, exocrine secretory epithelial cells, hormone secreting cells, epithelial cells, neural or sensory cells, photoreceptor cells, muscle cells, extracellular matrix cells, blood cells, cardiovascular cells, endothelial cells, vascular smooth muscle cells, kidney cells, pancreatic cells, immune cells, stem cells, germ cells, interstitial cells, stellate cells liver cells, gastrointestinal cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblasts, Schwann cells, adipose cells, bone cells, bone marrow cells, cartilage cells, pericytes, mesothelial cells, cells derived from endocrine tissue, stromal cells, progenitor cells, lymph cells, endoderm-derived cells, ectoderm-derived cells, mesoderm-derived cells, pericytes, chondroblasts, mesenchymal stem cells, connective tissue fibroblasts, tendon fibroblasts, bone marrow reticular tissue fibroblasts, non-epithelial fibroblasts, pericytes, osteoprogenitor cells, osteoblasts, osteoclasts, articular chondrocytes, stem cells, progenitor cells, totipotent cells, pluripotent stem cells, multipotent stem cells, induced pluripotent stem cells, and cells derived from any of the foregoing. Cells can be derived from, for example, mice, rats, pigs, sheep, goats, monkeys, or humans.

A percentage of the cells of a vascular graft disclosed herein can be viable. In some embodiments, about 50%, about 60%, about 70%, about 80%, about 90%, or about 100% of the cells of a vascular graft are viable. In some embodiments, about 50%-about 60%, about 50%-about 70%, about 50%-about 80%, about 50%-90%, about 50%-about 100%, about 60%-about 70%, about 60%-about 80%, about 60%-about 90%, about 60%-about 100%, about 70%-about 80%, about 70%-about 90%, about 70%-about 100%, about 80%-about 90%, about 80%-about 100%, or about 90%-about 100% of cells of a vascular graft disclosed herein are viable. In some embodiments, at least about 50%, at least about 60%, at least about 70%, at least about 80%, or at least about 90% of cells of a vascular graft disclosed herein are viable.

In some embodiments, a vascular graft disclosed herein comprises lithium phenyl 2-4-6 trimethylbenzoylphosphinate (LAP). The of LAP can protect the cells from free radical damage, harmful wavelengths, and photoinitators, which can be used to crosslink ECM materials. In some embodiments, the presence of LAP in an ECM material (e.g., Matrigel®) or in media increases polymerization rates, providing cell encapsulation at reduced initiator concentrations and therefore increased cell viability.

Dimensions

The diameter of the lumen of a primary channel (luminal diameter) can affect the flow of fluid through a vascular graft. In some embodiments, a vascular graft disclosed herein has a primary channel with a luminal diameter of about 1 cm to about 10 cm. In some embodiments, a vascular graft disclosed herein has a primary channel with a luminal diameter of about 1 cm to about 1.5 cm, about 1 cm to about 2 cm, about 1 cm to about 2.5 cm, about 1 cm to about 3 cm, about 1 cm to about 3.5 cm, about 1 cm to about 4 cm, about 1 cm to about 4.5 cm, about 1 cm to about 5 cm, about 1 cm to about 10 cm, about 1.5 cm to about 2 cm, about 1.5 cm to about 2.5 cm, about 1.5 cm to about 3 cm, about 1.5 cm to about 3.5 cm, about 1.5 cm to about 4 cm, about 1.5 cm to about 4.5 cm, about 1.5 cm to about 5 cm, about 1.5 cm to about 10 cm, about 2 cm to about 2.5 cm, about 2 cm to about 3 cm, about 2 cm to about 3.5 cm, about 2 cm to about 4 cm, about 2 cm to about 4.5 cm, about 2 cm to about 5 cm, about 2 cm to about 10 cm, about 2.5 cm to about 3 cm, about 2.5 cm to about 3.5 cm, about 2.5 cm to about 4 cm, about 2.5 cm to about 4.5 cm, about 2.5 cm to about 5 cm, about 2.5 cm to about 10 cm, about 3 cm to about 3.5 cm, about 3 cm to about 4 cm, about 3 cm to about 4.5 cm, about 3 cm to about 5 cm, about 3 cm to about 10 cm, about 3.5 cm to about 4 cm, about 3.5 cm to about 4.5 cm, about 3.5 cm to about 5 cm, about 3.5 cm to about 10 cm, about 4 cm to about 4.5 cm, about 4 cm to about 5 cm, about 4 cm to about 10 cm, about 4.5 cm to about 5 cm, about 4.5 cm to about 10 cm, or about 5 cm to about 10 cm. In some embodiments, a vascular graft disclosed herein has a primary channel with a luminal diameter of about 1 cm, about 1.5 cm, about 2 cm, about 2.5 cm, about 3 cm, about 3.5 cm, about 4 cm, about 4.5 cm, about 5 cm, or about 10 cm. In some embodiments, a vascular graft disclosed herein has a primary channel with a luminal diameter of at least about 1 cm, at least about 1.5 cm, at least about 2 cm, at least about 2.5 cm, at least about 3 cm, at least about 3.5 cm, at least about 4 cm, at least about 4.5 cm, or at least about 5 cm. In some embodiments, a vascular graft disclosed herein has a primary channel with a luminal diameter of at most about 1.5 cm, at most about 2 cm, at most about 2.5 cm, at most about 3 cm, at most about 3.5 cm, at most about 4 cm, at most about 4.5 cm, at most about 5 cm, or at most about 10 cm.

The luminal diameter of a secondary channel can also affect the flow of fluid through a vascular graft. In some embodiments, a vascular graft disclosed herein has a secondary channel with a luminal diameter of about 1 cm to about 10 cm. In some embodiments, a vascular graft disclosed herein has a secondary channel with a luminal diameter of about 1 cm to about 1.5 cm, about 1 cm to about 2 cm, about 1 cm to about 2.5 cm, about 1 cm to about 3 cm, about 1 cm to about 3.5 cm, about 1 cm to about 4 cm, about 1 cm to about 4.5 cm, about 1 cm to about 5 cm, about 1 cm to about 10 cm, about 1.5 cm to about 2 cm, about 1.5 cm to about 2.5 cm, about 1.5 cm to about 3 cm, about 1.5 cm to about 3.5 cm, about 1.5 cm to about 4 cm, about 1.5 cm to about 4.5 cm, about 1.5 cm to about 5 cm, about 1.5 cm to about 10 cm, about 2 cm to about 2.5 cm, about 2 cm to about 3 cm, about 2 cm to about 3.5 cm, about 2 cm to about 4 cm, about 2 cm to about 4.5 cm, about 2 cm to about 5 cm, about 2 cm to about 10 cm, about 2.5 cm to about 3 cm, about 2.5 cm to about 3.5 cm, about 2.5 cm to about 4 cm, about 2.5 cm to about 4.5 cm, about 2.5 cm to about 5 cm, about 2.5 cm to about 10 cm, about 3 cm to about 3.5 cm, about 3 cm to about 4 cm, about 3 cm to about 4.5 cm, about 3 cm to about 5 cm, about 3 cm to about 10 cm, about 3.5 cm to about 4 cm, about 3.5 cm to about 4.5 cm, about 3.5 cm to about 5 cm, about 3.5 cm to about 10 cm, about 4 cm to about 4.5 cm, about 4 cm to about 5 cm, about 4 cm to about 10 cm, about 4.5 cm to about 5 cm, about 4.5 cm to about 10 cm, or about 5 cm to about 10 cm. In some embodiments, a vascular graft disclosed herein has a secondary channel with a luminal diameter of about 1 cm, about 1.5 cm, about 2 cm, about 2.5 cm, about 3 cm, about 3.5 cm, about 4 cm, about 4.5 cm, about 5 cm, or about 10 cm. In some embodiments, a vascular graft disclosed herein has a secondary channel with a luminal diameter of at least about 1 cm, at least about 1.5 cm, at least about 2 cm, at least about 2.5 cm, at least about 3 cm, at least about 3.5 cm, at least about 4 cm, at least about 4.5 cm, or at least about 5 cm. In some embodiments, a vascular graft disclosed herein has a secondary channel with a luminal diameter of at most about 1.5 cm, at most about 2 cm, at most about 2.5 cm, at most about 3 cm, at most about 3.5 cm, at most about 4 cm, at most about 4.5 cm, at most about 5 cm, or at most about 10 cm.

The wall of a primary or secondary channel can comprise an inner wall and an outer wall to form a void space within the channel. The thickness of a void space (also referred to as channel wall thickness) can refer to the distance between the inner wall and the outer wall of the channel. In some embodiments, the channel wall thickness is about 1 mm to about 2 cm. In some embodiments, the channel wall thickness of a primary or secondary channel is about 1 mm to about 2 mm, about 1 mm to about 3 mm, about 1 mm to about 4 mm, about 1 mm to about 5 mm, about 1 mm to about 1 cm, about 1 mm to about 1.5 cm, about 1 mm to about 2 cm, about 2 mm to about 3 mm, about 2 mm to about 4 mm, about 2 mm to about 5 mm, about 2 mm to about 1 cm, about 2 mm to about 1.5 cm, about 2 mm to about 2 cm, about 3 mm to about 4 mm, about 3 mm to about 5 mm, about 3 mm to about 1 cm, about 3 mm to about 1.5 cm, about 3 mm to about 2 cm, about 4 mm to about 5 mm, about 4 mm to about 1 cm, about 4 mm to about 1.5 cm, about 4 mm to about 2 cm, about 5 mm to about 1 cm, about 5 mm to about 1.5 cm, about 5 mm to about 2 cm, about 1 cm to about 1.5 cm, about 1 cm to about 2 cm, or about 1.5 cm to about 2 cm. In some embodiments, the channel wall thickness of a primary or secondary channel is about 1 mm, about 2 mm, about 3 mm, about 4 mm, about 5 mm, about 1 cm, about 1.5 cm, or about 2 cm. In some embodiments, the channel wall thickness of a primary or secondary channel is at least about 1 mm, at least about 2 mm, at least about 3 mm, at least about 4 mm, at least about 5 mm, at least about 1 cm, or at least about 1.5 cm. In some embodiments, the channel wall thickness of a primary or secondary channel is at most about 2 mm, at most about 3 mm, at most about 4 mm, at most about 5 mm, at most about 1 cm, at most about 1.5 cm, or at most about 2 cm.

The flow of fluid through a vascular graft can be affected by the luminal diameter of a microstructure forming a cylindrical tube. In some embodiments, a microstructure forming a cylindrical tube has a luminal diameter of about 1 mm to about 2 mm. In some embodiments, a microstructure forming a cylindrical tube has a luminal diameter of about 1 mm to about 1.1 mm, about 1 mm to about 1.2 mm, about 1 mm to about 1.3 mm, about 1 mm to about 1.4 mm, about 1 mm to about 1.5 mm, about 1 mm to about 1.6 mm, about 1 mm to about 1.7 mm, about 1 mm to about 1.8 mm, about 1 mm to about 1.9 mm, about 1 mm to about 2 mm, about 1.1 mm to about 1.2 mm, about 1.1 mm to about 1.3 mm, about 1.1 mm to about 1.4 mm, about 1.1 mm to about 1.5 mm, about 1.1 mm to about 1.6 mm, about 1.1 mm to about 1.7 mm, about 1.1 mm to about 1.8 mm, about 1.1 mm to about 1.9 mm, about 1.1 mm to about 2 mm, about 1.2 mm to about 1.3 mm, about 1.2 mm to about 1.4 mm, about 1.2 mm to about 1.5 mm, about 1.2 mm to about 1.6 mm, about 1.2 mm to about 1.7 mm, about 1.2 mm to about 1.8 mm, about 1.2 mm to about 1.9 mm, about 1.2 mm to about 2 mm, about 1.3 mm to about 1.4 mm, about 1.3 mm to about 1.5 mm, about 1.3 mm to about 1.6 mm, about 1.3 mm to about 1.7 mm, about 1.3 mm to about 1.8 mm, about 1.3 mm to about 1.9 mm, about 1.3 mm to about 2 mm, about 1.4 mm to about 1.5 mm, about 1.4 mm to about 1.6 mm, about 1.4 mm to about 1.7 mm, about 1.4 mm to about 1.8 mm, about 1.4 mm to about 1.9 mm, about 1.4 mm to about 2 mm, about 1.5 mm to about 1.6 mm, about 1.5 mm to about 1.7 mm, about 1.5 mm to about 1.8 mm, about 1.5 mm to about 1.9 mm, about 1.5 mm to about 2 mm, about 1.6 mm to about 1.7 mm, about 1.6 mm to about 1.8 mm, about 1.6 mm to about 1.9 mm, about 1.6 mm to about 2 mm, about 1.7 mm to about 1.8 mm, about 1.7 mm to about 1.9 mm, about 1.7 mm to about 2 mm, about 1.8 mm to about 1.9 mm, about 1.8 mm to about 2 mm, or about 1.9 mm to about 2 mm. In some embodiments, a microstructure forming a cylindrical tube has a luminal diameter of about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm. In some embodiments, a microstructure forming a cylindrical tube has a luminal diameter of at least about 1 mm, at least about 1.1 mm, at least about 1.2 mm, at least about 1.3 mm, at least about 1.4 mm, at least about 1.5 mm, at least about 1.6 mm, at least about 1.7 mm, at least about 1.8 mm, or at least about 1.9 mm. In some embodiments, a microstructure forming the cylindrical tube has a luminal diameter of at most about 1.1 mm, at most about 1.2 mm, at most about 1.3 mm, at most about 1.4 mm, at most about 1.5 mm, at most about 1.6 mm, at most about 1.7 mm, at most about 1.8 mm, at most about 1.9 mm, or at most about 2 mm.

The wall of a microstructure forming a cylindrical tube can comprise an inner wall and an outer wall. The distance from the inner wall to the outer wall of a microstructure forming the cylindrical tube can be referred to as the thickness of the wall. In some embodiments, a microstructure forming the cylindrical tube has a wall with a thickness of about 0.1 mm to about 1 mm. In some embodiments, a microstructure forming the cylindrical tube has a wall with a thickness of about 0.1 mm to about 0.2 mm, about 0.1 mm to about 0.3 mm, about 0.1 mm to about 0.4 mm, about 0.1 mm to about 0.5 mm, about 0.1 mm to about 0.6 mm, about 0.1 mm to about 0.7 mm, about 0.1 mm to about 0.8 mm, about 0.1 mm to about 0.9 mm, about 0.1 mm to about 1 mm, about 0.2 mm to about 0.3 mm, about 0.2 mm to about 0.4 mm, about 0.2 mm to about 0.5 mm, about 0.2 mm to about 0.6 mm, about 0.2 mm to about 0.7 mm, about 0.2 mm to about 0.8 mm, about 0.2 mm to about 0.9 mm, about 0.2 mm to about 1 mm, about 0.3 mm to about 0.4 mm, about 0.3 mm to about 0.5 mm, about 0.3 mm to about 0.6 mm, about 0.3 mm to about 0.7 mm, about 0.3 mm to about 0.8 mm, about 0.3 mm to about 0.9 mm, about 0.3 mm to about 1 mm, about 0.4 mm to about 0.5 mm, about 0.4 mm to about 0.6 mm, about 0.4 mm to about 0.7 mm, about 0.4 mm to about 0.8 mm, about 0.4 mm to about 0.9 mm, about 0.4 mm to about 1 mm, about 0.5 mm to about 0.6 mm, about 0.5 mm to about 0.7 mm, about 0.5 mm to about 0.8 mm, about 0.5 mm to about 0.9 mm, about 0.5 mm to about 1 mm, about 0.6 mm to about 0.7 mm, about 0.6 mm to about 0.8 mm, about 0.6 mm to about 0.9 mm, about 0.6 mm to about 1 mm, about 0.7 mm to about 0.8 mm, about 0.7 mm to about 0.9 mm, about 0.7 mm to about 1 mm, about 0.8 mm to about 0.9 mm, about 0.8 mm to about 1 mm, or about 0.9 mm to about 1 mm. In some embodiments, a microstructure forming a cylindrical tube has wall with a thickness of about 0.1 mm, about 0.2 mm, about 0.3 mm, about 0.4 mm, about 0.5 mm, about 0.6 mm, about 0.7 mm, about 0.8 mm, about 0.9 mm, or about 1 mm. In some embodiments, a microstructure forming a cylindrical tube has wall with a thickness of at least about 0.1 mm, at least about 0.2 mm, at least about 0.3 mm, at least about 0.4 mm, at least about 0.5 mm, at least about 0.6 mm, at least about 0.7 mm, at least about 0.8 mm, or at least about 0.9 mm. In some embodiments, a microstructure forming a cylindrical tube has wall with a thickness of at most about 0.2 mm, at most about 0.3 mm, at most about 0.4 mm, at most about 0.5 mm, at most about 0.6 mm, at most about 0.7 mm, at most about 0.8 mm, at most about 0.9 mm, or at most about 1 mm.

In some embodiments, the wall of a primary channel, secondary channel, or a cylindrical tube forming a microstructure can comprise microchannels. Microchannels within the wall of a primary channel, the wall of a secondary channel, or the wall of a cylindrical tube forming a microstructure can be the same size or different sizes. In some embodiments, a microchannel has a diameter of about 1 μm to about 1 mm. In some embodiments, a microchannel has a diameter of about 1 μm to about 10 μm, about 1 μm to about 50 μm, about 1 μm to about 100 μm, about 1 μm to about 200 μm, about 1 μm to about 300 μm, about 1 μm to about 400 μm, about 1 μm to about 500 μm, about 10 μm to about 50 μm, about 10 μm to about 100 μm, about 10 μm to about 200 μm, about 10 μm to about 300 μm, about 10 μm to about 400 μm, about 10 μm to about 500 μm, about 10 μm to about 1 mm, about 50 μm to about 100 μm, about 50 μm to about 200 μm, about 50 μm to about 300 μm, about 50 μm to about 400 μm, about 50 μm to about 500 μm, about 50 μm to about 1 mm, about 100 μm to about 200 μm, about 100 μm to about 300 μm, about 100 μm to about 400 μm, about 100 μm to about 500 μm, about 100 μm to about 1 mm, about 200 μm to about 300 μm, about 200 μm to about 400 μm, about 200 μm to about 500 μm, about 200 μm to about 1 mm, about 300 μm to about 400 μm, about 300 μm to about 500 μm, about 300 μm to about 1 mm, about 400 μm to about 500 μm, about 400 μm to about 1 mm, or about 500 μm to about 1 mm. In some embodiments, a microchannel has a diameter of about 1 μm, about 10 μm, about 50 μm, about 100 μm, about 200 μm, about 300 μm, about 400 μm, about 500 μm, or about 1 mm. In some embodiments, a microchannel has a diameter of at least about 1 μm, at least about 10 μm, at least about 50 μm, at least about 100 μm, at least about 200 μm, at least about 300 μm, at least about 400 μm, or at least about 500 μm. In some embodiments, a microchannel has a diameter of at most about 10 μm, at most about 50 μm, at most about 100 μm, at most about 200 μm, at most about 300 μm, at most about 400 μm, at most about 500 μm, or at most about 1 mm.

Bioprinting

Disclosed herein is a method of printing a vascular graft. In some embodiments, the printing is three-dimensional (3D) printing. In some embodiments, the method comprises depositing material through a needle onto a substrate via an extruder. The material can be a polymeric material. In some embodiments, the polymeric material is biocompatible and/or biodegradable. Non-limiting examples of polymeric materials that can be deposited include polyesters, poly (alpha-hydroxy acids), polylactones, polyorthoesters, polycarbonates, polyanhydrides, polyphosphazenes, polycaprolactone (PCL), poly lactic acid (PLA), poly L-lactide-glycolic acid (PLGA), poly ethylene glycol diacrylate (PEGDA), polyethylene glycol (PEG), poly(hydroxyethyl methacrylate) (PHEMA), polyvinyl alcohol (PVA), polyvinylpyrrolidone (PVP), carboxymethyl cellulose (CMC), polyimide (PI), polyacrylate (PAA), polyurethane (PU), PEG-lactide, and PEG-glycolide. In some embodiments, 1, 2, 3, 4, 5, 6, 7, 8, 9, 10, 11, 12, 13, 14, 15 or more polymeric materials is deposited. In some embodiments, a mixture of 1, 2, 3, 4, 5, 6, 7, 8, 9, 10, 11, 12, 13, 14, 15 or more polymeric materials are deposited.

A method of the disclosure can comprise depositing an ECM material onto a substrate by an extrusion based bioprinting process. In some embodiments, an ECM material and a polymeric material are deposited. Non-limiting examples of ECM materials include Matrigel®, carrageenan, carbopol, chitosan, sodium alga acid, collagen I, collagen III, collagen IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, collagen type XIX, collagen type XX, collagen type XXI, collagen type XXII, collagen type XXIII, collagen type XXIV, collagen type XXV, collagen type XXVI, collagen type XXVII, collagen type XXVIII, collagen type XXIX, chondroitin sulfate, dextrose, fibrin, fibrinogen, gelatin, gelose, gelatin methacrylate, hyaluronic acid, heparin sulfate, laminin, polyethylene glycol, a glycosaminoglycan (GAG), a proteoglycan, or a combination thereof.

A method of the disclosure can comprise crosslinking a polymeric material. Crosslinking of a polymeric material can occur after deposition on a substrate or during the deposition process. Crosslinking of a polymeric material can comprise, for example, crosslinking with a free radical initiator, crosslinking with thiol or amine moieties, and/or delivering a crosslinking reagent to the polymeric material. Non-limiting examples of crosslinking reagents include calcium (Ca'), magnesium (Mg'), calcium chloride, calcium sulfate, calcium carbonate, glutaraldehyde, genipin, nordihydroguaiaretic acid, tannin acid, procyanidin, 1-ethyl-3-3-dimethylaminopropylcarbodiimide hydrochloride (EDC), divinyl benzene (DVB), ethylene glycol dimethacrylate (EGDMA), tetraethylene glycol diacrylate (TEGDA), polyethylene glycol diacrylate (PEGDA), and combinations thereof. Additionally, a polymeric material can be crosslinked via exposure to light. In some embodiments, a photoinitiator is added to a polymeric material prior to crosslinking via exposure to light. Non-limiting examples of photoinitiators include (2-hydroxy-1-[4-(2-hydroxyethoxy)phenyl]-2-methyl-1-propanone; lithium phenyl-2,4,6-trimethylbenzoylphosphinate (LAP); (2,2'-azobis[2-methyl-N-(2-hydroxyethyl)propionamide]; 2-isocyanotoethyl methacrylate; benzoyl benzylamine; camphorquinone; thiol-norbornene (thiol-ene); riboflavin; lucirin-TPO; Rose Bengal/furfuryl; ethyl eosin; methacrylic anhydride; 2,2-dimethoxy-2-phenylacetophenone; and Eosin Y.

In some embodiments, a method of the disclosure comprises depositing an ECM material mixed with cells so that the resulting vascular graft contains ECM material embedded with cells. Non-limiting examples of cells that can be deposited with an ECM material include chondrogenic cells, chondrocytes, chondroprogenitor cells, chondrogenic precursors, keratinocytes, hair root cells, hair shaft cells, hair matrix cells, exocrine secretory epithelial cells, hormone secreting cells, epithelial cells, neural or sensory cells, photoreceptor cells, muscle cells, extracellular matrix cells, blood cells, cardiovascular cells, endothelial cells, vascular smooth muscle cells, kidney cells, pancreatic cells, immune cells, stem cells, germ cells, interstitial cells, stellate cells liver cells, gastrointestinal cells, lung cells, tracheal cells, vascular cells, skeletal muscle cells, cardiac cells, skin cells, smooth muscle cells, connective tissue cells, corneal cells, genitourinary cells, breast cells, reproductive cells, endothelial cells, epithelial cells, fibroblasts, Schwann cells, adipose cells, bone cells, bone marrow cells, cartilage cells, pericytes, mesothelial cells, cells derived from endocrine tissue, stromal cells, progenitor cells, lymph cells, endoderm-derived cells, ectoderm-derived cells, mesoderm-derived cells, pericytes, chondroblasts, mesenchymal stem cells, connective tissue fibroblasts, tendon fibroblasts, bone marrow reticular tissue fibroblasts, non-epithelial fibroblasts, pericytes, osteoprogenitor cells, osteoblasts, osteoclasts, articular chondrocytes, stem cells, progenitor cells, totipotent cells, pluripotent stem cells, multipotent stem cells, induced pluripotent stem cells, and cells derived from any of the foregoing.

In some embodiments, a method of the disclosure comprises printing a vascular graft in the form of a hollow cylindrical vessel comprising a plurality of viable cells embedded in an ECM material. For example, the method can comprise depositing a polymeric material, a plurality of types of viable cells, and an ECM material in layers onto or within a substrate. The substrate can be, for example, a dish, a petri dish, a tissue culture plate, a cell culture flask, a peel-off flask, jar, or a perfusable chip.

A method of the disclosure can print a vascular graft comprising channel walls with microchannels. Microchannels can be generated using a fugitive ink. Non-limiting examples of fugitive inks include Pluronic® F-127 (PF127), gelatin, and carbohydrate glass. Fugitive inks are inks designed to be removable upon an introduction of a stimuli, including, for example, submersion in a liquid, an increase in temperature, or a decrease in temperature. In some embodiments, a method disclosed herein comprises printing a fugitive ink into a material, and then removing the fugitive ink by submerging the material in an aqueous solution leaving behind a microchannel. Pluronic® F127 is composed of a hydrophobic poly(propylene oxide) (PPO) segment and two hydrophilic poly(ethylene oxide) (PEO) segments arranged in a PEO-PPO-PEO configuration.

Microchannels can be generated by, for example, pre-printing the polymer material, e.g., PCL, with a fugitive ink or by printing the polymer material first, and then printing the fugitive ink on top. In some embodiments, PCL and PF127 are printed together followed by adding cells to a mixture composed of LAP and Matrigel® and incorporating the cell mixture into the vascular graft. In some embodiments, PCL and PF127 are printed together followed by printing a cell infused mixture of LAP and Matrigel®. In some embodiments, PCL is printed separately and PF127 is added on top of the PCL followed by printing of a cell infused LAP and Matrigel® layer. In some embodiments, PCL is printed with Matrigel® and cells to which PF127 is subsequently added as a top layer along with cell infused LAP.

Bioprinting Parameters

A method disclosed herein can utilize a needle in a bioprinting process. In some embodiments, one or more polymeric materials, fugitive inks, ECM materials, cell suspensions, or a combination thereof is deposited through a needle onto a substrate. A method of the disclosure can print from more than one needle, for example, 1, 2, 3, 4, 5, 6, 7, 8, 9, 10, 11, 12, 13, 14, 15 or more needles. In some embodiments, a needle used in a method disclosed herein has a diameter that is expressed using the Birmingham gauge system. In some embodiments, a needle has a diameter of 7 gauge, 8 gauge, 9 gauge, 10 gauge, 11 gauge, 12 gauge, 13 gauge, 14 gauge, 15 gauge, 16 gauge, 17 gauge, 18 gauge, 19 gauge, 20 gauge, 21 gauge, 22 gauge, 22s gauge, 23 gauge, 24 gauge, 25 gauge, 26 gauge, 26s gauge, 27 gauge, 28 gauge, 29 gauge, 30 gauge, 31 gauge, 32 gauge, 33 gauge, or 34 gauge.

In some embodiments, a needle of the disclosure has a diameter of between 0.1 mm to 400 mm. In some embodiments, a needle of the disclosure has a diameter of between 0.1 mm to 0.5 mm, between 0.1 mm to 1 mm, between 0.1 mm to 10 mm, between 0.1 mm to 20 mm, between 0.1 mm to 30 mm, between 0.1 mm to 40 mm, between 0.1 mm to 50 mm, between 0.1 mm to 100 mm, between 0.1 mm to 200 mm, between 0.1 mm to 300 mm, between 0.1 mm to 400 mm, between 0.5 mm to 1 mm, between 0.5 mm to 10 mm, between 0.5 mm to 20 mm, between 0.5 mm to 30 mm, between 0.5 mm to 40 mm, between 0.5 mm to 50 mm, between 0.5 mm to 100 mm, between 0.5 mm to 200 mm, between 0.5 mm to 300 mm, between 0.5 mm to 400 mm, between 1 mm to 10 mm, between 1 mm to 20 mm, between 1 mm to 30 mm, between 1 mm to 40 mm, between 1 mm to 50 mm, between 1 mm to 100 mm, between 1 mm to 200 mm, between 1 mm to 300 mm, between 1 mm to 400 mm, between 10 mm to 20 mm, between 10 mm to 30 mm, between 10 mm to 40 mm, between 10 mm to 50 mm, between 10 mm to 100 mm, between 10 mm to 200 mm, between 10 mm to 300 mm, between 10 mm to 400 mm, between 20 mm to 30 mm, between 20 mm to 40 mm, between 20 mm to 50 mm, between 20 mm to 100 mm, between 20 mm to 200 mm, between 20 mm to 300 mm, between 20 mm to 400 mm, between 30 mm to 40 mm, between 30 mm to 50 mm, between 30 mm to 100 mm, between 30 mm to 200 mm, between 30 mm to 300 mm, between 30 mm to 400 mm, between 40 mm to 50 mm, between 40 mm to 100 mm, between 40 mm to 200 mm, between 40 mm to 300 mm, between 40 mm to 400 mm, between 50 mm to 100 mm, between 50 mm to 200 mm, between 50 mm to 300 mm, between 50 mm to 400 mm, between 100 mm to 200 mm, between 100 mm to 300 mm, between 100 mm to 400 mm, between 200 mm to 300 mm, between 200 mm to 400 mm, or between 300 mm to 400 mm. In some embodiments, a needle of the disclosure has a diameter of 0.1 mm, 0.5 mm, 1 mm, 10 mm, 20 mm, 30 mm, 40 mm, 50 mm, 100 mm, 200 mm, 300 mm, or 400 mm. In some embodiments, a needle of the disclosure has a diameter of at least 0.1 mm, at least 0.5 mm, at least 1 mm, at least 10 mm, at least 20 mm, at least 30 mm, at least 40 mm, at least 50 mm, at least 100 mm, at least 200 mm, or at least 300 mm. In some embodiments, a needle of the disclosure has a diameter of at most 0.5 mm, at most 1 mm, at most 10 mm, at most 20 mm, at most 30 mm, at most 40 mm, at most 50 mm, at most 100 mm, at most 200 mm, at most 300 mm, or at most 400 mm.

A method of the disclosure can deposit a cell infused mixture. A cell infused mixture of the disclosure can have a cell density of, for example, about 1 cell/μL, about 10 cells/μL, about 100 cells/μL, about 1 cell/nL, about 10 cells/nL, about 100 cells/nL, about 1 cell/μL, about 10 cells/μL, about 100 cells/μL, about 1000 cells/μL, about 10,000 cells cells/μL, about 100,000 cells/μL. In some embodiments, the cell density of a cell infused mixture of the disclosure is about $2\times10^6$ cells/mL, about $3\times10^6$ cells/mL, about $4\times10^6$ cells/mL, about $5\times10^6$ cells/mL, about $6\times10^6$ cells/mL, about $7\times10^6$ cells/mL, about $8\times10^6$ cells/mL, about $9\times10^6$ cells/mL, about $10\times10^6$ cells/mL, about $15\times10^6$ cells/mL, about $20\times10^6$ cells/mL, about $25\times10^6$ cells/mL, about $30\times10^6$ cells/mL, about $35\times10^6$ cells/mL, about $40\times10^6$ cells/mL, about $45\times10^6$ cells/mL, or about $50\times10^6$ cells/mL. A cell infused mixture can comprise one, or more than one cell type. For example, a cell infused mixture of the disclosure contains, in some embodiments, 1, 2, 3, 4, 5, 6, 7, 8, 9, 10, 12, 13, 14, 15, or more cell types.

In some embodiments, a method of the disclosure can generate a vascular graft by printing multiple layers. For example, a method of the disclosure can print a polymeric material layer, an ECM material layer, a cell infused layer, a cell infused-ECM layer, a fugitive ink layer, and/or a layer comprising a combination of any of the forgoing. In some embodiments, the method comprises printing 2, 3, 4, 5, 6, 7, 8, 9, 10, 20, 30, 40, 50, 100 or more layers. In some embodiments, the thickness of each layer is about 0.01 mm to about 10 mm. In some embodiments, the thickness of each layer is about 0.01 mm to about 0.05 mm, about 0.01 mm to about 0.1 mm, about 0.01 mm to about 0.25 mm, about 0.01 mm to about 0.5 mm, about 0.01 mm to about 1 mm, about 0.01 mm to about 2 mm, about 0.01 mm to about 3 mm, about 0.01 mm to about 4 mm, about 0.01 mm to about 5 mm, about 0.01 mm to about 10 mm, about 0.05 mm to about 0.1 mm, about 0.05 mm to about 0.25 mm, about 0.05 mm to about 0.5 mm, about 0.05 mm to about 1 mm, about 0.05 mm to about 2 mm, about 0.05 mm to about 3 mm, about 0.05 mm to about 4 mm, about 0.05 mm to about 5 mm, about 0.05 mm to about 10 mm, about 0.1 mm to about 0.25 mm, about 0.1 mm to about 0.5 mm, about 0.1 mm to about 1 mm, about 0.1 mm to about 2 mm, about 0.1 mm to about 3 mm, about 0.1 mm to about 4 mm, about 0.1 mm to about 5 mm, about 0.1 mm to about 10 mm, about 0.25 mm to about 0.5 mm, about 0.25 mm to about 1 mm, about 0.25 mm to about 2 mm, about 0.25 mm to about 3 mm, about 0.25 mm to about 4 mm, about 0.25 mm to about 5 mm, about 0.25 mm to about 10 mm, about 0.5 mm to about 1 mm, about 0.5 mm to about 2 mm, about 0.5 mm to about 3 mm, about 0.5 mm to about 4 mm, about 0.5 mm to about 5 mm, about 0.5 mm to about 10 mm, about 1 mm to about 2 mm, about 1 mm to about 3 mm, about 1 mm to about 4 mm, about 1 mm to about 5 mm, about 1 mm to about 10 mm, about 2 mm to about 3 mm, about 2 mm to about 4 mm, about 2 mm to about 5 mm, about 2 mm to about 10 mm, about 3 mm to about 4 mm, about 3 mm to about 5 mm, about 3 mm to about 10 mm, about 4 mm to about 5 mm, about 4 mm to about 10 mm, or about 5 mm to about 10 mm. In some embodiments, the thickness of each layer is about 0.01 mm, about 0.05 mm, about 0.1 mm, about 0.25 mm, about 0.5 mm, about 1 mm, about 2 mm, about 3 mm, about 4 mm, about 5 mm, or about 10 mm. In some embodiments, the thickness of each layer is at least about 0.01 mm, at least about 0.05 mm, at least about 0.1 mm, at least about 0.25 mm, at least about 0.5 mm, at least about 1 mm, at least about 2 mm, at least about 3 mm, at least about 4 mm, or at least about 5 mm. In some embodiments, the thickness of each layer is at most about 0.05 mm, at most about 0.1 mm, at most about 0.25 mm, at most about 0.5 mm, at most about 1 mm, at most about 2 mm, at most about 3 mm, at most about 4 mm, at most about 5 mm, or at most about 10 mm.

A method disclosed herein can comprise using an extruder to pass a material through a needle and onto a substrate. In some embodiments, multiple extruders deposit one or more materials onto a substrate. For example, multiple extruders can deposit material simultaneously, sequentially, or via a predefined sequence. In some embodiments, deposition from one or more extruders is controlled in real time. In some embodiments, printing is performed with 1, 2, 3, 4, 5, 6, 7, 8, 9, 10, 11, 12, 13, 14, 15, or more extruders.

The temperature at which an extruder operates can be controlled. In some embodiments, an extruder operates at a temperature of about 25° C. to about 200° C. In some embodiments, an extruder operates at a temperature of about 25° C. to about 37° C., about 25° C. to about 50° C., about 25° C. to about 75° C., about 25° C. to about 100° C., about 25° C. to about 150° C., about 25° C. to about 200° C., about 27° C. to about 37° C., about 27° C. to about 50° C., about 27° C. to about 75° C., about 27° C. to about 100° C., about 27° C. to about 150° C., about 27° C. to about 200° C., about 37° C. to about 50° C., about 37° C. to about 75° C., about 37° C. to about 100° C., about 37° C. to about 150° C., about 37° C. to about 200° C., about 50° C. to about 75° C., about 50° C. to about 100° C., about 50° C. to about 150° C., about 50° C. to about 200° C., about 75° C. to about 100° C., about 75° C. to about 150° C., about 75° C. to about 200° C., about 100° C. to about 150° C., about 100° C. to about 200° C., or about 150° C. to about 200° C. In some embodiments, an extruder operates at a temperature of about 25° C. about 27° C., about 37° C., about 50° C., about 75° C., about 100° C., about 150° C., or about 200° C. In some embodiments, an extruder operates at a temperature of at least about 25° C., at least about 27° C., at least about 37° C., at least about 50° C., at least about 75° C., at least about 100° C., or at least about 150° C. In some embodiments, an extruder operates at a temperature of at most about 25° C., at most about 37° C., at most about 50° C., at most about 75° C., at most about 100° C., at most about 150° C., or at most about 200° C.

In some embodiments, pressurized air is used to move a material through an extruder. The air pressure of an extruder can be controlled. In some embodiments, an extruder operates at an air pressure of about 600 kPa to about 800 kPa. In some embodiments, an extruder operates at an air pressure of about 600 kPa to about 625 kPa, about 600 kPa to about 650 kPa, about 600 kPa to about 675 kPa, about 600 kPa to about 700 kPa, about 600 kPa to about 725 kPa, about 600 kPa to about 750 kPa, about 600 kPa to about 775 kPa, about 600 kPa to about 800 kPa, about 625 kPa to about 650 kPa, about 625 kPa to about 675 kPa, about 625 kPa to about 700 kPa, about 625 kPa to about 725 kPa, about 625 kPa to about 750 kPa, about 625 kPa to about 775 kPa, about 625 kPa to about 800 kPa, about 650 kPa to about 675 kPa, about 650 kPa to about 700 kPa, about 650 kPa to about 725 kPa, about 650 kPa to about 750 kPa, about 650 kPa to about 775 kPa, about 650 kPa to about 800 kPa, about 675 kPa to about 700 kPa, about 675 kPa to about 725 kPa, about 675 kPa to about 750 kPa, about 675 kPa to about 775 kPa, about 675 kPa to about 800 kPa, about 700 kPa to about 725 kPa, about 700 kPa to about 750 kPa, about 700 kPa to about 775 kPa, about 700 kPa to about 800 kPa, about 725 kPa to about 750 kPa, about 725 kPa to about 775 kPa, about 725 kPa to about 800 kPa, about 750 kPa to about 775 kPa, about 750 kPa to about 800 kPa, or about 775 kPa to about 800 kPa. In some embodiments, an extruder operates at an air pressure of about 600 kPa, about 625 kPa, about 650 kPa, about 675 kPa, about 689.5 kPa, about 700 kPa, about 717.1 kPa, about 725 kPa, about 750 kPa, about 775 kPa, or about 800 kPa. In some embodiments, an extruder operates at an air pressure of at least about 600 kPa, at least about 625 kPa, at least about 650 kPa, at least about 675 kPa, at least about 700 kPa, at least about 725 kPa, at least about 750 kPa, or at least about 775 kPa. In some embodiments, an extruder operates at an air pressure of at most about 625 kPa, at most about 650 kPa, at most about 675 kPa, at most about 700 kPa, at most about 725 kPa, at most about 750 kPa, at most about 775 kPa, or at most about 800 kPa.

In some embodiments, an extruder operates at an air pressure of about 87 pounds per square inch (psi) to about 116 psi. In some embodiments, an extruder operates at an air pressure of about 87 psi to about 90.6 psi, about 87 psi to about 94.3 psi, about 87 psi to about 97.9 psi, about 87 psi to about 101.5 psi, about 87 psi to about 105.2 psi, about 87 psi to about 108.8 psi, about 87 psi to about 112.4 psi, about 87 psi to about 116 psi, about 90.6 psi to about 94.3 psi, about 90.6 psi to about 97.9 psi, about 90.6 psi to about 101.5 psi, about 90.6 psi to about 105.2 psi, about 90.6 psi to about 108.8 psi, about 90.6 psi to about 112.4 psi, about 90.6 psi to about 116 psi, about 94.3 psi to about 97.9 psi, about 94.3 psi to about 101.5 psi, about 94.3 psi to about 105.2 psi, about 94.3 psi to about 108.8 psi, about 94.3 psi to about 112.4 psi, about 94.3 psi to about 116 psi, about 97.9 psi to about 101.5 psi, about 97.9 psi to about 105.2 psi, about 97.9 psi to about 108.8 psi, about 97.9 psi to about 112.4 psi, about 97.9 psi to about 116 psi, about 101.5 psi to about 105.2 psi, about 101.5 psi to about 108.8 psi, about 101.5 psi to about 112.4 psi, about 101.5 psi to about 116 psi, about 105.2 psi to about 108.8 psi, about 105.2 psi to about 112.4 psi, about 105.2 psi to about 116 psi, about 108.8 psi to about 112.4 psi, about 108.8 psi to about 116 psi, or about 112.4 psi to about 116 psi. In some embodiments, an extruder operates at an air pressure of about 87 psi, about 90.6 psi, about 94.3 psi, about 97.9 psi, about 100 psi, about 101.5 psi, about 104 psi, about 105.2 psi, about 108.8 psi, about 112.4 psi, or about 116 psi. In some embodiments, an extruder operates at an air pressure of at least about 87 psi, at least about 90.6 psi, at least about 94.3 psi, at least about 97.9 psi, at least about 101.5 psi, at least about 105.2 psi, at least about 108.8 psi, or at least about 112.4 psi. In some embodiments, an extruder operates at an air pressure of at most about 90.6 psi, at most about 94.3 psi, at most about 97.9 psi, at most about 101.5 psi, at most about 105.2 psi, at most about 108.8 psi, at most about 112.4 psi, or at most about 116 psi.

A method of the disclosure can comprise printing a material at various linear extrusion speeds. In some embodiments, material is deposited at a linear extrusion speed of about 100 mm/s to about 800 mm/s. In some embodiments, material is deposited at a linear extrusion speed of about 100 mm/s to about 150 mm/s, about 100 mm/s to about 200 mm/s, about 100 mm/s to about 250 mm/s, about 100 mm/s to about 300 mm/s, about 100 mm/s to about 350 mm/s, about 100 mm/s to about 400 mm/s, about 100 mm/s to about 450 mm/s, about 100 mm/s to about 500 mm/s, about 100 mm/s to about 600 mm/s, about 100 mm/s to about 700 mm/s, about 100 mm/s to about 800 mm/s, about 150 mm/s to about 200 mm/s, about 150 mm/s to about 250 mm/s, about 150 mm/s to about 300 mm/s, about 150 mm/s to about 350 mm/s, about 150 mm/s to about 400 mm/s, about 150 mm/s to about 450 mm/s, about 150 mm/s to about 500 mm/s, about 150 mm/s to about 600 mm/s, about 150 mm/s to about 700 mm/s, about 150 mm/s to about 800 mm/s, about 200 mm/s to about 250 mm/s, about 200 mm/s to about 300 mm/s, about 200 mm/s to about 350 mm/s, about 200 mm/s to about 400 mm/s, about 200 mm/s to about 450 mm/s, about 200 mm/s to about 500 mm/s, about 200 mm/s to about 600 mm/s, about 200 mm/s to about 700 mm/s, about 200 mm/s to about 800 mm/s, about 250 mm/s to about 300 mm/s, about 250 mm/s to about 350 mm/s, about 250 mm/s to about 400 mm/s, about 250 mm/s to about 450 mm/s, about 250 mm/s to about 500 mm/s, about 250 mm/s to about 600 mm/s, about 250 mm/s to about 700 mm/s, about 250 mm/s to about 800 mm/s, about 300 mm/s to about 350 mm/s, about 300 mm/s to about 400 mm/s, about 300 mm/s to about 450 mm/s, about 300 mm/s to about 500 mm/s, about 300 mm/s to about 600 mm/s, about 300 mm/s to about 700 mm/s, about 300 mm/s to about 800 mm/s, about 350 mm/s to about 400 mm/s, about 350 mm/s to about 450 mm/s, about 350 mm/s to about 500 mm/s, about 350 mm/s to about 600 mm/s, about 350 mm/s to about 700 mm/s, about 350 mm/s to about 800 mm/s, about 400 mm/s to about 450 mm/s, about 400 mm/s to about 500 mm/s, about 400 mm/s to about 600 mm/s, about 400 mm/s to about 700 mm/s, about 400 mm/s to about 800 mm/s, about 450 mm/s to about 500 mm/s, about 450 mm/s to about 600 mm/s, about 450 mm/s to about 700 mm/s, about 450 mm/s to about 800 mm/s, about 500 mm/s to about 600 mm/s, about 500 mm/s to about 700 mm/s, about 500 mm/s to about 800 mm/s, about 600 mm/s to about 700 mm/s, about 600 mm/s to about 800 mm/s, or about 700 mm/s to about 800 mm/s. In some embodiments, material is deposited at a linear extrusion speed of about 100 mm/s, about 150 mm/s, about 200 mm/s, about 250 mm/s, about 300 mm/s, about 350 mm/s, about 400 mm/s, about 450 mm/s, about 500 mm/s, about 600 mm/s, about 700 mm/s, or about 800 mm/s. In some embodiments, material is deposited at a linear extrusion speed of at least about 100 mm/s, at least about 150 mm/s, at least about 200 mm/s, at least about 250 mm/s, at least about 300 mm/s, at least about 350 mm/s, at least about 400 mm/s, at least about 450 mm/s, at least about 500 mm/s, at least about 600 mm/s, or at least about 700 mm/s. In some embodiments, material is deposited at a linear extrusion speed of at most about 150 mm/s, at most about 200 mm/s, at most about 250 mm/s, at most about 300 mm/s, at most about 350 mm/s, at most about 400 mm/s, at most about 450 mm/s, at most about 500 mm/s, at most about 600 mm/s, at most about 700 mm/s, or at most about 800 mm/s.

A method of the disclosure can comprise printing a material at various volumetric speeds. In some embodiments, the printing occurs with a volumetric speed of about 1 µL/s to about 100 µL/s. In some embodiments, the printing occurs with a volumetric speed of about 1 µL/s to about 5 µL/s, about 1 µL/s to about 10 µL/s, about 1 µL/s to about 15 µL/s, about 1 µL/s to about 20 µL/s, about 1 µL/s to about 25 µL/s, about 1 µL/s to about 50 µL/s, about 1 µL/s to about 100 µL/s, about 5 µL/s to about 10 µL/s, about 5 µL/s to about 15 µL/s, about 5 µL/s to about 20 µL/s, about 5 µL/s to about 25 µL/s, about 5 µL/s to about 50 µL/s, about 5 µL/s to about 100 µL/s, about 10 µL/s to about 15 µL/s, about 10 µL/s to about 20 µL/s, about 10 µL/s to about 25 µL/s, about 10 µL/s to about 50 µL/s, about 10 µL/s to about 100 µL/s, about 15 µL/s to about 20 µL/s, about 15 µL/s to about 25 µL/s, about 15 µL/s to about 50 µL/s, about 15 µL/s to about 100 µL/s, about 20 µL/s to about 25 µL/s, about 20 µL/s to about 50 µL/s, about 20 µL/s to about 100 µL/s, about 25 µL/s to about 50 µL/s, about 25 µL/s to about 100 µL/s, or about 50 µL/s to about 100 µL/s. In some embodiments, the printing occurs with a volumetric speed of about 1 µL/s, about 5 µL/s, about 10 µL/s, about 15 µL/s, about 20 µL/s, about 25 µL/s, about 50 µL/s, or about 100 µL/s. In some embodiments, the printing occurs with a volumetric speed of at least about 1 µL/s, at least about 5 µL/s, at least about 10 µL/s, at least about 15 µL/s, at least about 20 µL/s, at least about 25 µL/s, or at least about 50 µL/s. In some embodiments, the printing occurs with a volumetric speed of at most about 5 µL/s, at most about 10 µL/s, at most about 15 µL/s, at most about 20 µL/s, at most about 25 µL/s, at most about 50 µL/s, or at most about 100 µL/s.

A method of the disclosure can comprise controlling the deposition of materials with a degree of resolution. In some embodiments, a method disclosed herein can control material deposition with a resolution of about 0.01 mm to about 1 mm. In some embodiments, a method disclosed herein can control material deposition with a resolution of about 0.01 mm to about 0.05 mm, about 0.01 mm to about 0.1 mm, about 0.01 mm to about 0.2 mm, about 0.01 mm to about 0.3 mm, about 0.01 mm to about 0.4 mm, about 0.01 mm to about 0.5 mm, about 0.01 mm to about 1 mm, about 0.05 mm to about 0.1 mm, about 0.05 mm to about 0.2 mm, about 0.05 mm to about 0.3 mm, about 0.05 mm to about 0.4 mm, about 0.05 mm to about 0.5 mm, about 0.05 mm to about 1 mm, about 0.1 mm to about 0.2 mm, about 0.1 mm to about 0.3 mm, about 0.1 mm to about 0.4 mm, about 0.1 mm to about 0.5 mm, about 0.1 mm to about 1 mm, about 0.2 mm to about 0.3 mm, about 0.2 mm to about 0.4 mm, about 0.2 mm to about 0.5 mm, about 0.2 mm to about 1 mm, about 0.3 mm to about 0.4 mm, about 0.3 mm to about 0.5 mm, about 0.3 mm to about 1 mm, about 0.4 mm to about 0.5 mm, about 0.4 mm to about 1 mm, or about 0.5 mm to about 1 mm. In some embodiments, a method disclosed herein can control material deposition with a resolution of about 0.01 mm, about 0.05 mm, about 0.1 mm, about 0.2 mm, about 0.3 mm, about 0.4 mm, about 0.5 mm, or about 1 mm. In some embodiments, a method disclosed herein can control material deposition with a resolution of at least about 0.01 mm, at least about 0.05 mm, at least about 0.1 mm, at least about 0.2 mm, at least about 0.3 mm, at least about 0.4 mm, or at least about 0.5 mm. In some embodiments, a method disclosed herein can control material deposition with a resolution of at most about 0.05 mm, at most about 0.1 mm, at most about 0.2 mm, at most about 0.3 mm, at most about 0.4 mm, at most about 0.5 mm, or at most about 1 mm.

Computer System

Bioprinting parameters such as, for example, deposition speed, extruder pressure, extruder temperature, extruder deposition patterns, the location of deposition, layer thickness, and the material deposited can be controlled by a computer system. In some embodiments, the computer system comprises a processor, a memory device, an operating system, and a software module for monitoring or operating the extruder. In some embodiments, the computer system comprises a digital processing device and includes one or more hardware central processing units (CPU). In further embodiments, the computer system includes an operating system configured to perform executable instructions. In some embodiments, the operating system is software, including programs and data, which manages the device's hardware and provides services for execution of applications. Suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. In some embodiments a mobile smart phone operating system is used. Non-limiting examples of mobile smart phone operating systems include Nokia® Symbian® OS, Apple® iOS®, Research In Motion® BlackBerry OS®, Google® Android®, Microsoft® Windows Phone® OS, Microsoft® Windows Mobile® OS, Linux, and Palm® WebOS. In some embodiments, the computer system includes a storage and/or memory device. In some embodiments, the storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the device is a storage device including, by way of non-limiting examples, CD-ROMs, DVDs, flash memory devices, magnetic disk drives, magnetic tapes drives, optical disk drives, and cloud computing-based storage. In some embodiments, the storage and/or memory device is a combination of devices such as those disclosed herein.

In some embodiments, the computer systems described herein include user interfaces. In further embodiments, the user interfaces include graphic user interfaces (GUIs), such as a Repetier-Host graphical user interface. In still further embodiments, the user interfaces are interactive and present a user with menus and options for interacting with the computer systems and delivery systems described herein. In further embodiments, the computer system includes a display screen to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In some embodiments, an OLED display is a passive-matrix OLED (PMOLED) or active-matrix OLED (AMOLED) display. In some embodiments, the display is a plasma display. In some embodiments, the display is a video projector. In some embodiments, the display is a combination of displays such as those disclosed herein. In some embodiments, the device includes an input device to receive information from a user. In some embodiments, the input device is a keyboard. In some embodiments, the input device is a key pad. In some embodiments, the input device is the display screen, which is a touch screen or a multi-touch screen. In some embodiments, the input device is a microphone to capture voice or other sound input. In some embodiments, the systems, and software modules disclosed herein are intranet-based. In some embodiments, the systems and software modules are Internet-based. In some embodiments, the computer systems and software modules are World Wide Web-based. In some embodiments, the computer systems and software modules are cloud computing-based. In some embodiments, the computer systems and software modules are based on data storage devices including, by way of non-limiting examples, CD-ROMs, DVDs, flash memory devices, RAM (e.g., DRAM, SRAM, etc.), ROM (e.g., PROM, EPROM, EEPROM, etc.), magnetic tape drives, magnetic disk drives, optical disk drives, magneto-optical drives, solid-state drives, and combinations thereof.

EXAMPLES

Example 1: Vascular Construct with a Bifurcated Primary Channel

Figure 2:
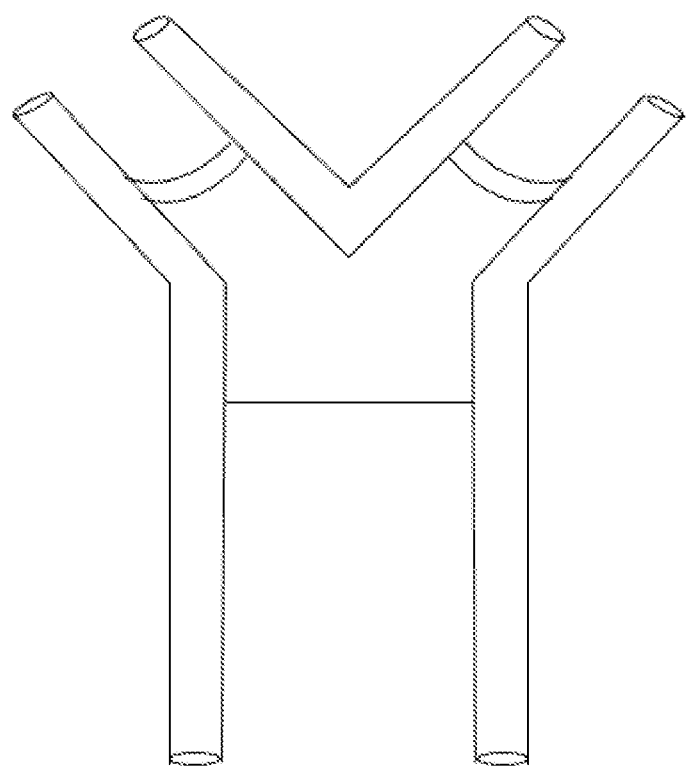
FIG. 2 shows a cross sectional view of a vascular construct containing a bifurcation in the primary channel.

A schematic showing a cross-sectional view of a primary channel is shown in FIG. 1. The lumen of the channel is formed by the channel wall, which is made up of a polymeric material. The channel wall comprises an inner wall and an outer wall to create a void space within the channel wall. As can also be seen in FIG. 1, the void space is filled with Matrigel® which can be used to culture viable cells. The primary channel contains a bifurcation and forms a vascular construct. A schematic showing a cross-sectional view of a vascular construct with a bifurcated primary channel is shown in FIG. 2.

Example 2: Branched Vascular Construct with a Bifurcated Primary Channel

Figure 3:
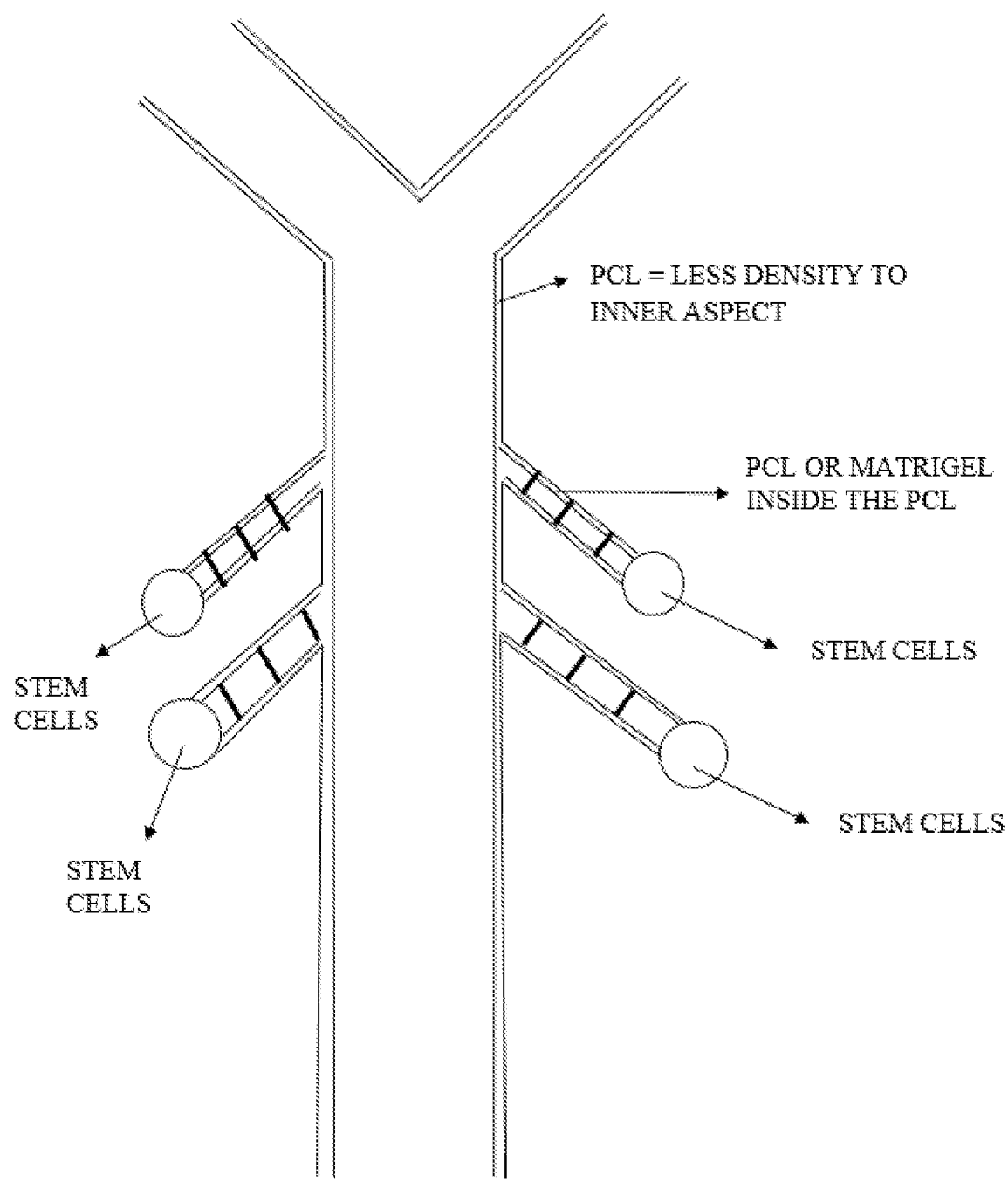
FIG. 3 shows a cross-sectional view from the side of a vascular construct containing a bifurcation in the primary channel and a plurality of branches emanating from the primary channel. PCL=polycaprolactone.
Figure 4:
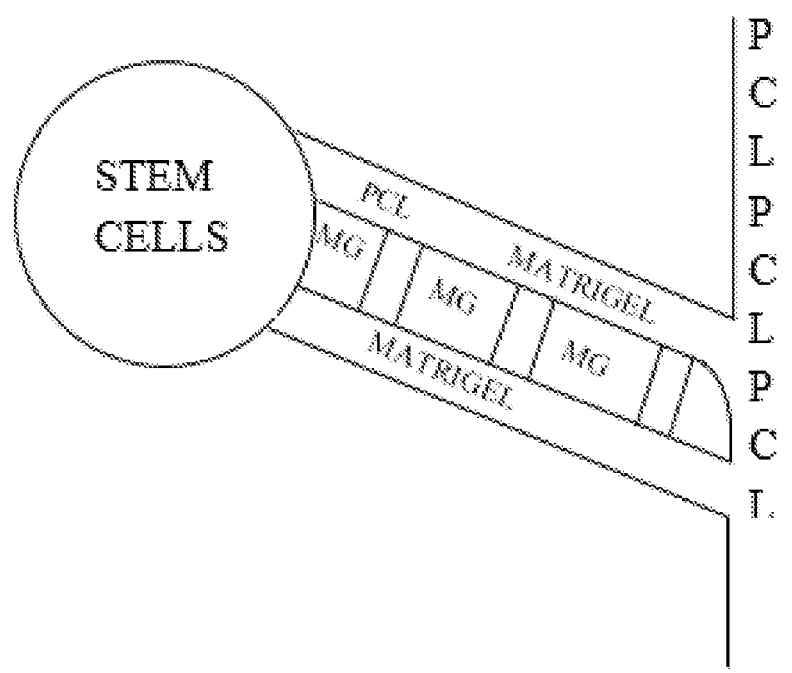
FIG. 4 shows branching structures in which the walls of the branch are comprise a mixture of the polymeric material and a cell infused extracellular matrix material. MG=Matrigel®.
Figure 5:
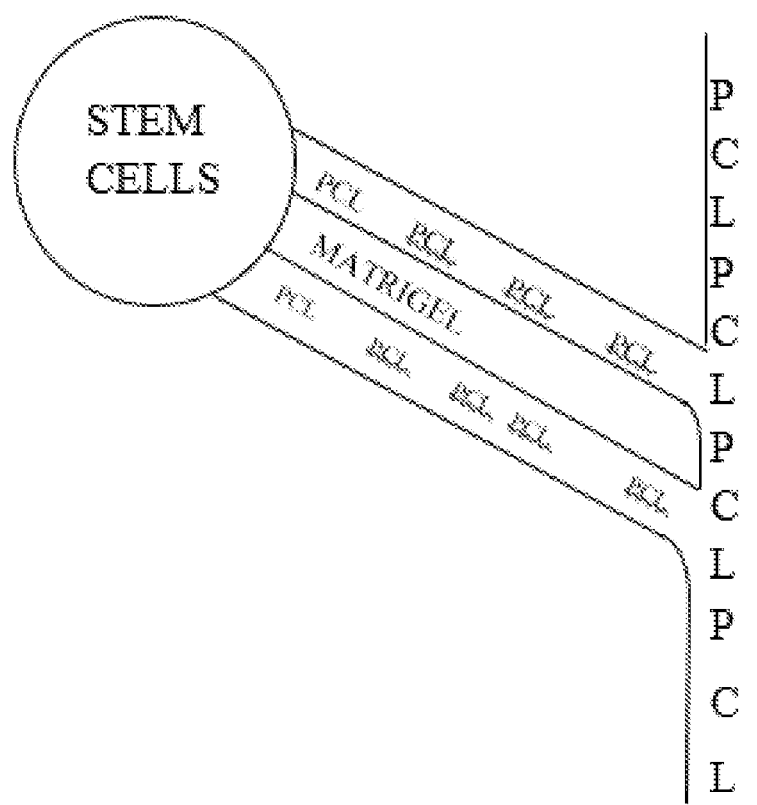
FIG. 5 shows branching structures in which the walls of the branch comprise a polymeric material surrounding a central core of an extracellular matrix material. PCL=polycaprolactone.

FIG. 3 shows a schematic of a cross-sectional view of a vascular construct containing a bifurcated primary channel with a plurality of branches emanating from the primary channel. The walls of the primary channel are made up of PCL. At the end of each branch is a spheroid of stem cells. The branch walls are composed of a mixture of PCL and cell infused Matrigel® surrounding a central core of Matrigel® as shown in FIG. 4 (MG=Matrigel®). Alternatively, the branch walls are composed of PCL surrounding a central core of Matrigel® as shown in FIG. 5.

Example 3: Microstructure Design of Channel Walls

Figure 6:
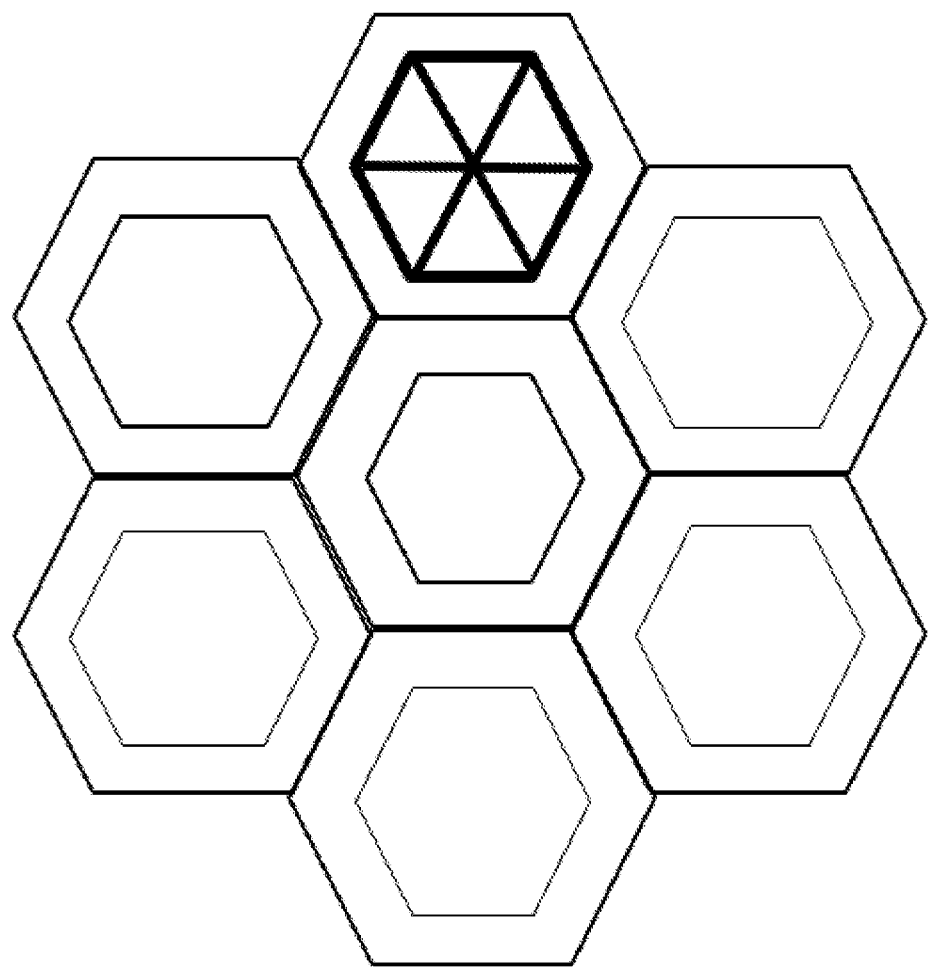
FIG. 6 shows the honeycomb microstructure of cylindrical tubes forming the walls of a primary channel.
Figure 7:
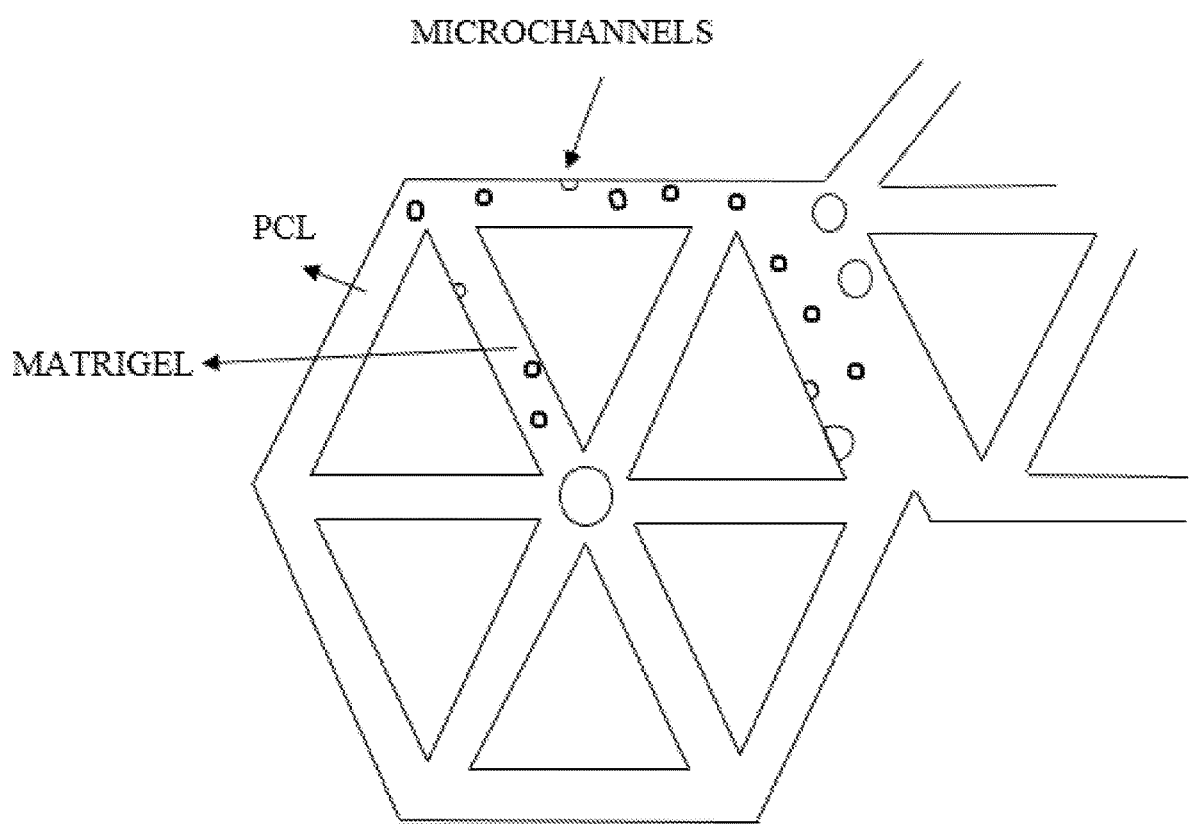
FIG. 7 shows a cylindrical tube with triangular substructures that forms a microstructure.

A primary channel is formed by walls containing a honeycomb microstructure. A schematic of a honeycomb microstructure is shown in FIG. 6. The microstructure is formed by six hollow cylindrical PCL tubes connected in a hexagonal matter around a central PCL tube. Some of the tubes of the microstructure contain microchannels and triangular sub-structures within the hollow spaces of the tubes as shown in FIG. 7. Cell infused Matrigel® is printed into the triangular sub-structures and within hollow spaces of the tubes.

Example 4: Cylindrical Tube with Microchannels

Figure 8:
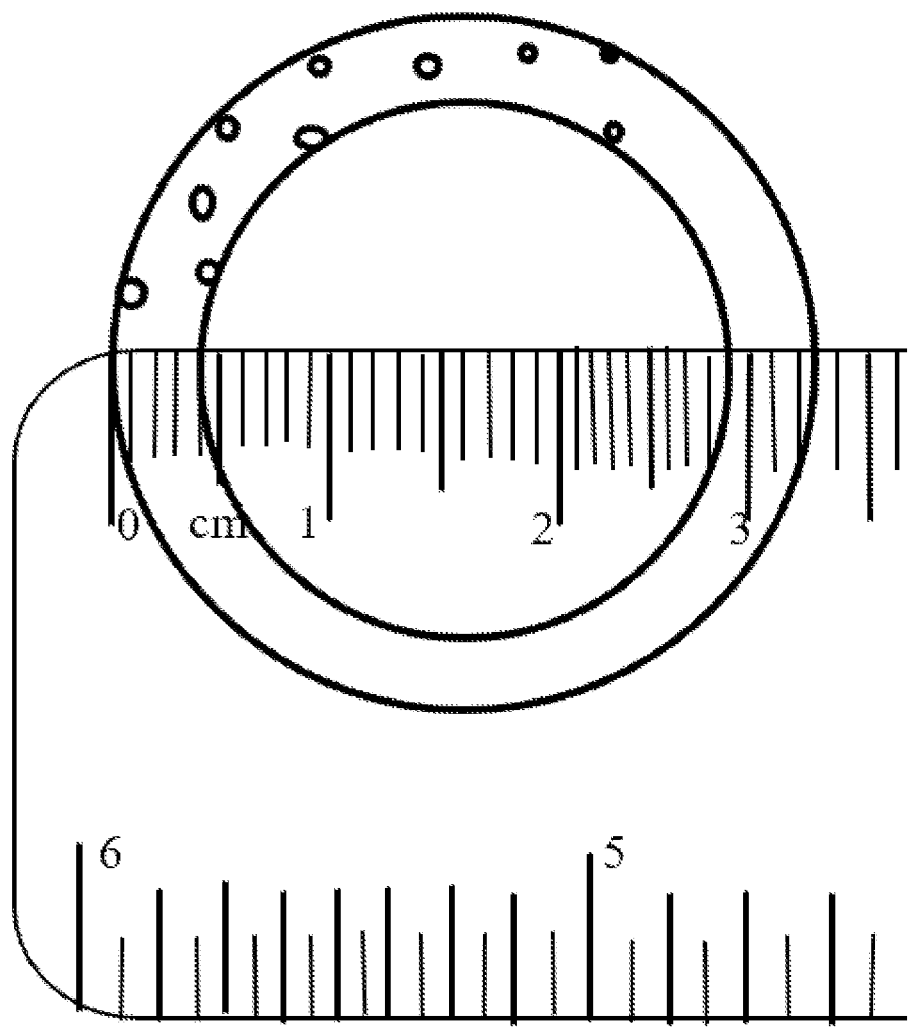
FIG. 8 shows a cross-section of a cylindrical tube forming the wall of a primary channel.

FIG. 8. shows a schematic of a cross-sectional view of a cylindrical tube that forms the wall of a primary channel. The tube contains microchannels (depicted by small circles). The tubes have an outside diameter of about 3.3 cm, an inner diameter of about 2.5 cm, a thickness of about 0.4 cm, a distance from the inner wall to the center of about 1.3 cm, a distance of the outer wall to the center of about 1.7 cm, and a height of about 4 cm.

Example 5: Bioprinting of a Vascular Graft

A vascular graft is printed via an extrusion-based bioprinting process. STL files are created with a computer-aided design (CAD) program that incorporates G codes. STL files contain designs for the vascular graft and are created with a Repetier-Host graphical user interface. Multiple syringe-based extruder uses air compression to move a plunger from a 10 mL syringe at a resolution of 100 micron. At the tip is a needle. Each extruder is separately controlled via software and features such as deposit size, speed of deposition, and extrusion temperature are controlled individually.

The vascular graft is printed onto a peel-off flask. A PCL-PF127 mixture is used to print a vascular graft with a hollow cylindrical vessel comprising a primary channel having a plurality of cylindrical branches extending therefrom. The cylindrical channel walls contain microstructures generated using a fugitive ink composed of PF127. Multipotent stem cells are then added to a mixture of LAP and Matrigel®. The mixture is deposited as a layer of the walls of the cylindrical branches. Multipotent stem cell spheroids are attached to the distal ends of the cylindrical branches. The vascular graft is submerged in Dulbecco's Modified Eagle Media (DMEM) with 10% fetal bovine serum and 1% penicillin/streptomycin for one week to culture cells. Cell viability is tested using a CellTiter-Glo®. A vascular graft submerged in methanol is used as a positive control for cell death. As a negative control for cell death, cells are cultured on tissue culture plastic. The number of cells that is seeded on the tissue culture plastic is the same number of cells that are deposited into the vascular graft.

Example 6 Implantation of a Vascular Graft

A PCL-Matrigel® mixture is used to print a vascular graft with a hollow cylindrical vessel comprising a single primary channel. The channel walls contain endothelial cell-embedded Matrigel® within a void space. The vascular graft is cultured for one week. Following graft culture, the vascular graft is implanted into a patient with atherosclerotic plaque build up in a coronary artery. A patient is place under anesthesia. An incision is made in the patient's chest and the sternum is cut to provide access to the heart. The patient is then placed on a heart lung machine for the duration of the surgery. A blood vessel upstream of the atherosclerotic plaque build-up is cut and attached to one end of the vascular graft. A second portion of the blood vessel located downstream of the atherosclerotic plaque build-up is cut and connected to the other end of the vascular graft, allowing blood flow to bypass the blockage caused by the atherosclerotic plaque. Implantation of the vascular graft improves blood flow to the patient's cardiac muscle and decreases the risk of heart attack.

EMBODIMENTS

The following non-limiting embodiments provide illustrative examples of the methods and systems disclosed of the disclosure, but do not limit the scope of the methods and systems of the disclosure.

Embodiment 1. A vascular graft comprising a cylindrical hollow body, wherein the cylindrical hollow body comprises a first opening and a second opening, and wherein the cylindrical hollow body comprises: (a) a primary channel, wherein the primary channel comprises an inner wall and an outer wall with a first void space between the inner wall and the outer wall, wherein the inner wall and the outer wall are composed of a polymer; and (b) a viable cell-infused extracellular matrix material disposed within the first void space, and wherein the first void space contains a microstructure containing a plurality of microchannels.

Embodiment 2. The vascular graft of embodiment 1, wherein the primary channel bifurcates at the second opening into two secondary channels.

Embodiment 3. The vascular graft of embodiment 1 or 2, wherein the polymer is biodegradable.

Embodiment 4. The vascular graft of any one of embodiments 1-3, wherein the polymer is biocompatible.

Embodiment 5. The vascular graft of any one of embodiments 1-4, wherein the polymer is polyester.

Embodiment 6. The vascular graft of any one of embodiments 1-4, wherein the polymer is polycaprolactone.

Embodiment 7. The vascular graft of any one of embodiments 1-6, wherein the cells of the viable cell-infused extracellular matrix material are stem cells.

Embodiment 8. The vascular graft of any one of embodiments 1-7, wherein the extracellular matrix material comprises a basement membrane matrix.

Embodiment 9. The vascular graft of any one of embodiments 1-8, wherein the plurality of microchannels within the microstructure of the first void space are arranged to form a regular pattern.

Embodiment 10. The vascular graft of embodiment 9, wherein the pattern is hexagonal.

Embodiment 11. The vascular graft of any one of embodiments 1-10, wherein the plurality of microchannels contain cells.

Embodiment 12. The vascular graft of any one of embodiments 1-11, wherein the primary channel has a luminal diameter of from about 1 cm to about 10 cm.

Embodiment 13. The vascular graft of any one of embodiments 1-12, wherein the first void space has a thickness of from about 1 mm to about 2 cm.

Embodiment 14. The vascular graft of any one of embodiments 1-13, wherein a diameter of one of the microchannels from the plurality of microchannels is from about 1 µm to about 500 µm.

Embodiment 15. The vascular graft of any one of embodiments 1-14, wherein the cylindrical hollow body comprises a first end and a second end, and the first opening is at the first end, and the second opening is at the second end, wherein the first opening and the second opening form a straight passage through the cylindrical hollow body.

Embodiment 16. The vascular graft of any one of embodiments 1-15, wherein the primary channel further contains a tertiary channel connected to the primary channel, wherein the tertiary channel comprises a distal end and a proximal end, wherein the proximal end is connected to the primary channel.

Embodiment 17. The vascular graft of embodiment 16, wherein the distal end of the tertiary channel comprises a spheroid of cells.

Embodiment 18. The vascular graft of embodiment 16 or 17, wherein the tertiary channel is a cylindrical hollow body comprising an inner wall and an outer wall to form a second void space, wherein the inner wall and the outer wall are composed of a polymer.

Embodiment 19. The vascular graft of embodiment 18, wherein a viable cell-infused extracellular matrix material is disposed within the second void space.

Embodiment 20. A vascular graft, the vascular graft comprising a cylindrical hollow body, wherein the cylindrical hollow body comprises a first opening and a second opening, and wherein the cylindrical hollow body comprises: (a) a primary channel, wherein the primary channel comprises an inner wall and an outer wall with a void space between the inner wall and the outer wall, wherein the inner wall and the outer wall are composed of a polymer; and (b) a viable cell-infused extracellular matrix material disposed within the void space, and wherein the void space contains a microstructure containing a plurality of microchannels, wherein the vascular graft is submerged in a media that promotes the growth of the cells in the viable cell-infused extracellular matrix material.

Embodiment 21. A method of increasing flow of a biological fluid in a vessel in a subject in need thereof, the method comprising implanting a vascular graft in the subject, wherein the vascular graft comprises a cylindrical hollow body, and wherein the cylindrical hollow body comprises: (a) a primary channel, wherein the primary channel comprises an inner wall and an outer wall with a void space between the inner wall and the outer wall, wherein the inner wall and the outer wall are composed of a polymer; and (b) a viable cell-infused extracellular matrix material disposed within the void space, and wherein the void space contains a microstructure containing a plurality of microchannels, wherein implantation of the vascular graft in the subject increases flow of the biological fluid in the vessel of the subject.

Embodiment 22. The method of embodiment 21, wherein the subject has a cardiovascular disease.

Embodiment 23. The method of embodiment 21 or 22, wherein the biological fluid is blood.

Embodiment 24. The method of any one of embodiments 21-23, wherein the vessel is an artery.

Embodiment 25. A method of printing a vascular graft, the method comprising: (a) depositing onto a substrate a polymer to form an inner wall; (b) depositing onto the inner wall a viable cell-infused extracellular matrix material; (c) depositing onto the viable cell-infused extracellular matrix material the polymer to form an outer wall, wherein the depositing of steps (a), (b), and (c) forms a cylindrical hollow body, wherein the cylindrical hollow body comprises a first opening and a second opening, and wherein the cylindrical hollow body comprises a primary channel, wherein the primary channel comprises the inner wall and the outer wall; and wherein the vascular graft is printed to provide a microstructure containing a plurality of microchannels in the void space.

Embodiment 26. The method of embodiment 25, the method further comprising submerging the substrate in a media that promotes growth of the cells in the viable cell-infused extracellular matrix material.

Embodiment 27. The method of embodiment 25 or 26, wherein the primary channel comprises a fugitive ink.

What is claimed is:

1. A method of printing a vascular graft, the method comprising:
    (a) depositing onto a substrate a first polymer to form an inner wall;
    (b) depositing onto the inner wall a polymer material to form a microstructure, wherein the microstructure comprises a hollow tube with a tube wall comprising a plurality of microchannels;
    (c) depositing a viable cell-infused extracellular matrix material to the microstructure; and
    (d) depositing onto the microstructure a second polymer to form an outer wall,
    wherein the depositing of steps (a)-(d) forms a cylindrical hollow body, wherein the cylindrical hollow body comprises a first opening and a second opening, and wherein the cylindrical hollow body comprises a primary channel, wherein the primary channel comprises the inner wall and the outer wall with a void space between the inner wall and the outer wall, wherein the void space comprises the microstructure.

2. The method of claim 1, wherein the primary channel bifurcates at the second opening into two secondary channels.

3. The method of claim 1, wherein the first polymer and the second polymer are the same.

4. The method of claim 1, wherein the first polymer and the second polymer are biodegradable.

5. The method of claim 1, wherein the first polymer and the second polymer are biocompatible.

6. The method of claim 1, wherein the first polymer is polyester.

7. The method of claim 1, wherein the first polymer is polycaprolactone.

8. The method of claim 1, wherein cells of the viable cell-infused extracellular matrix material are stem cells.

9. The method of claim 1, wherein the plurality of microchannels is arranged to form a regular pattern.

10. The method of claim 9, wherein the regular pattern is hexagonal.

11. The method of claim 1, wherein the primary channel has a luminal diameter of from 1 centimeter (cm) to 10 cm.

12. The method of claim 1, wherein the void space has a thickness of from 1 millimeter (mm) to 2 cm.

13. The method of claim 1, wherein a diameter of one of the plurality of microchannels is between 1 micrometer (µm) and 500 µm.

14. The method of claim 1, wherein the cylindrical hollow body comprises a first end and a second end, and the first opening is at the first end, and the second opening is at the second end, wherein the first opening and the second opening form a substantially straight passage through the cylindrical hollow body.

15. The method of claim 1, further comprising forming a tertiary channel connected to the primary channel, wherein the tertiary channel comprises a distal end and a proximal end, wherein the proximal end is connected to the primary channel.

16. The method of claim 15, wherein the distal end of the tertiary channel comprises a spheroid of cells.

17. The method of claim 15, wherein the tertiary channel is a cylindrical hollow body comprising an inner wall and an outer wall to form an additional void space, wherein the inner wall and the outer wall of the tertiary channel are composed of a polymer.

18. The method of claim 17, further comprising disposing an additional viable cell-infused extracellular matrix within the additional void space.

19. The method of claim 1, further comprising submerging the vascular graft in a media that promotes growth of cells in the viable cell-infused extracellular matrix material.

20. The method of claim 1, wherein the polymer material further comprises a fugitive ink, and wherein the method further comprises removing the fugitive ink to create the plurality of microchannels in the tube wall.

21. The method of claim 1, wherein the microstructure is a honeycomb microstructure.

* * * * *